United States Patent [19]

Gueremy et al.

[11] Patent Number: 5,114,949
[45] Date of Patent: May 19, 1992

[54] HETEROCYCLIC DERIVATIVES, THEIR PREPARATION AND MEDICINAL PRODUCTS CONTAINING THEM

[75] Inventors: Claude Gueremy, Houilles; Jean-Luc Malleron, Marcoussis; Serge Mignani, Livry-Gargan, all of France

[73] Assignee: Rhone-Poulenc Sante, Antony, France

[21] Appl. No.: 615,670

[22] Filed: Nov. 19, 1990

[30] Foreign Application Priority Data

Nov. 20, 1989 [FR] France ............... 89 15177
Dec. 26, 1989 [FR] France ............... 89 17164
Jun. 21, 1990 [FR] France ............... 90 07774

[51] Int. Cl.⁵ .................. A61K 31/44; A61K 31/445
[52] U.S. Cl. ................... 514/293; 514/255;
514/290; 514/291; 514/292; 514/294; 514/317;
514/320; 514/323; 514/324; 544/361; 544/362;
544/376; 546/83; 546/98; 546/198; 546/201;
546/205
[58] Field of Search ............. 546/118, 155, 83, 201,
546/98, 193, 198, 205; 514/303, 314, 320, 317,
290, 291, 292, 293, 294, 323

[56] References Cited

U.S. PATENT DOCUMENTS

| 4,110,449 | 8/1978 | Wade et al. | 424/250 |
| 4,416,888 | 11/1983 | Le Fur et al. | 546/201 |
| 4,710,500 | 12/1987 | Perregaard | 514/254 |

FOREIGN PATENT DOCUMENTS

| 0045024 | 2/1982 | European Pat. Off. | 546/201 |
| 200322 | 5/1986 | European Pat. Off. | |
| 2708913 | 9/1977 | Fed. Rep. of Germany | 546/201 |
| 2621588 | 4/1989 | France | |
| 63-301881A | 12/1988 | Japan | 546/201 |
| 1399608 | 7/1985 | United Kingdom | 546/201 |

OTHER PUBLICATIONS

European Search Report dated Jul. 10, 1990.
European Search Report dated Aug. 3, 1990.

*Primary Examiner*—Glennon H. Hollrah
*Assistant Examiner*—Shailendra Kamar
*Attorney, Agent, or Firm*—Morgan & Finnegan

[57] ABSTRACT

Compounds are disclosed of formula:

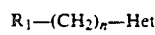

in which $R_1$ represents a residue of formula

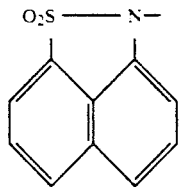

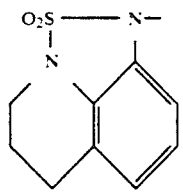

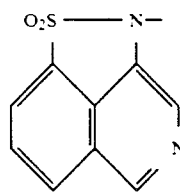

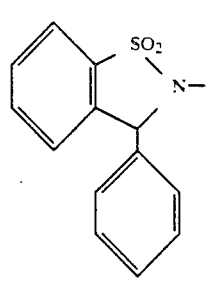

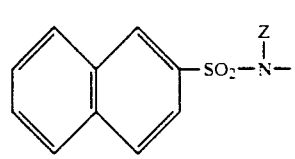

X represents a hydrogen atom or an alkyl radical,
Y represents a hydrogen atom or an alkyl or alkoxy radical,
Z represents an alkyl radical,
n is equal to 2 or 3,
Het represents a substituted piperidino (substituted at the 4-position with a 1-indenylidene, 1-indenyl or 1-indanyl radical or with a chain —(CH₂)ₘ—R₂ or =CH—R₂), substituted 1,2,3,6-tetrahydro-1-pyridyl (substituted at the 4-position with a chain —(CH₂)ₘ—R₂),
m is equal to 1 or 2, and
R₂ represents an optionally substituted 2- or 3-indolyl radical, a 1- or 2-indanyl, 1- or 2-indenyl, an optionally substituted 1,2,3,4-tetrahydro-5H-pyrido[4,3-b]indol-2-yl radical, a 1,2,3,4-tetrahydro-3-quinolyl radical, an optionally substituted 1,2,3,4-tetrahydro-2-naphthyl radical or a 1-indolyl radical, their preparation and medicinal products containing them.

6 Claims, No Drawings

HETEROCYCLIC DERIVATIVES, THEIR PREPARATION AND MEDICINAL PRODUCTS CONTAINING THEM

FIELD OF THE INVENTION

The present invention relates to compounds of formula:

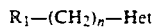  (I)

their preparation and to medicinal products containing them.

DESCRIPTION OF THE INVENTION

In the formula (I),
$R_1$ represents a residue of formula:

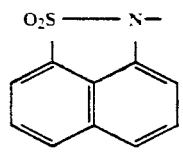 (A)

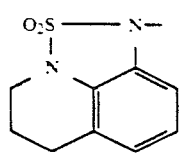 (B)

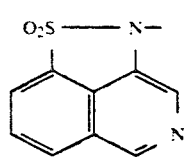 (C)

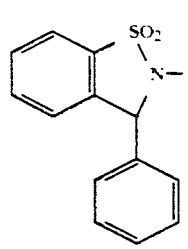 (D)

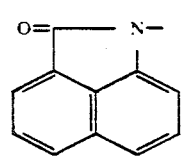 (E)

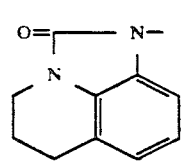 (F)

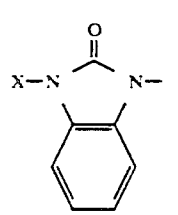 (G)

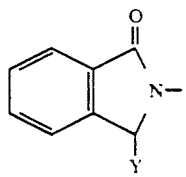 (H)

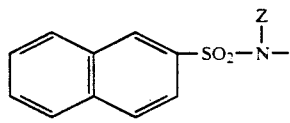 (J)

X represents a hydrogen atom or an alkyl radical,
Y represents a hydrogen atom or an alkyl or alkoxy radical,
Z represents an alkyl radical,
n is equal to 2 or 3,
Het represents a substituted piperidino (substituted at the 4-position with a 1-indenylidene, 1-indenyl or 1-indanyl radical or with a chain —$(CH_2)_m$—$R_2$ or =CH—$R_2$), substituted 1,2,3,6-tetrahydro-1-pyridyl (substituted at the 4-position with a chain —$(CH_2)_m$—$R_2$) or substituted 1-piperazinyl radical (substituted at the 4-position with a chain —$(CH_2)_m$—$R_2$),
m is equal to 1 or 2, and
$R_2$ represents a 2- or 3-indolyl (optionally substituted with a halogen atom and/or on the nitrogen atom with an alkyl radical), 1- or 2-indanyl, 1-or 2-indenyl, 3-quinolyl, 3-chromanyl, 1,2,3,4-tetrahydro-5H-pyrido[4,3-b]indol-2-yl, (optionally substituted with a halogen atom), 1,2,3,4-tetrahydro-3-quinolyl, 1,2,3,4-tetrahydro-2-naphthyl (optionally substituted with a halogen atom) or 1-indolyl radical.

In the foregoing definitions and those to be mentioned below, the alkyl and alkoxy radicals contain 1 to 4 carbon atoms in a straight or branched chain.

The invention also relates to the salts of the compounds of formula (I) with inorganic or organic acids.

In the formula (I), the halogen atoms are preferably fluorine atoms.

The compounds of formula (I) containing at least one asymmetric center possess isomeric forms. The racemates and enantiomers of these compounds also form part of the invention.

The compounds of formula (I), with the exception of those in which $R_1$ represents a residue of formula (G) in which X represents a hydrogen atom, may be prepared by the action of a halogenated derivative of formula:

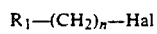  (II)

in which $R_1$ has the same meanings as above, n has the same meanings as in the formula (I) and Hal represents a halogen (preferably chlorine, bromine or iodine) atom, on a derivative of formula:

  (III)

in which Het has the same meanings as in formula (I).

This reaction is generally performed in an inert solvent such as tetrahydrofuran, dimethylformamide or a mixture of these solvents, in the presence of a base such as an alkali metal bicarbonate or a tertiary amine such as a trialkylamine, at the boiling point of the solvent.

The halogenated derivatives of formula (II) may be obtained by the action of a derivative of formula:

   (IV)

in which R₁ has the same meanings as above, on a dihalogenated derivative of formula:

   (V)

in which Hal and X represent a halogen (preferably chlorine, bromine or iodine) atom and n has the same meanings as in the formula (I).

This reaction is generally performed in an inert solvent such as dimethylformamide in the presence of sodium hydride, at a temperature between 20° C. and the boiling point of the solvent.

The derivatives of formula (IV) are marketed, or may be obtained by application or adaptation of the methods described in the examples.

The derivatives of formula (III) may be obtained by application or adaptation of the methods described by C. GUEREMY et al., J. Med. Chem., 23, 1306 (1980); C. S. RUNTY et al., Gazz. Chem. Ital., 81, 613 (1951); A. O. M. STOPPANI, Revista Argentina Microbiologica, 19, 121 (1987); C. GUEREMY et al., Patent EP 42.322; A. P. GRAY, J. Am. Chem. Soc., 79, 3554 (1957); R. T. BORCHARDT et al., J. Het. Chem., 24, 1499 (1987); V. SNIECKUS, Can. J. Chem., 51, 792 (1973); and in the examples.

The compounds of formula (I) for which R₁ represents a residue of formula (G) in which X represents a hydrogen atom may be prepared by the hydrolysis of a derivative of formula:

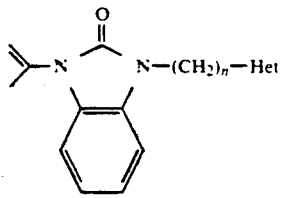   (VI)

in which n and Het have the same meanings as in the formula (I).

This hydrolysis is performed in an acid medium (e.g. sulphuric acid, hydrochloric acid) in an inert solvent such as an alcohol (e.g. methanol, ethanol) at a temperature between 20° C. and the boiling point of the solvent.

The compounds of formula (VI) may be obtained by application or adaptation of the method described in the examples.

The compounds of formula (I) for which R₂ represents a 2- or 3-indolyl radical substituted on the nitrogen atom with an alkyl radical and optionally substituted with a halogen atom may also be obtained by the alkylation of a corresponding compound of formula (I) for which R₂ represents a 2- or 3-indolyl radical optionally substituted with a halogen atom.

This alkylation is generally performed by means of an alkyl halide in the presence of a base such as an alkali metal hydride, in an inert solvent such as dimethylformamide, tetrahydrofuran or dioxane, at a temperature in the region of 20° C.

The compounds of formula (I) for which R₁ represents a residue of formula (H) in which Y represents a hydrogen atom may also be obtained by the reduction of a derivative of formula:

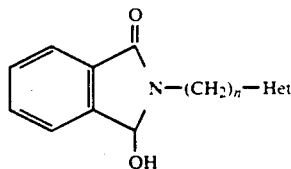   (VII)

in which n and Het have the same meanings as in the formula (I).

This reduction is preferably performed by means of a reducing agent such as zinc, in the presence of an acid such as acetic acid, at a temperature in the region of 120° C.

The compounds of formula (I) for which Het represents a piperidino substituted at the 4-position with a 1-indenylidene may also be obtained by the action of a compound of formula:

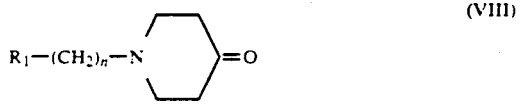   (VIII)

in which R₁ and n have the same meanings as in formula (I) on a metallic derivative of indene.

This reaction is generally performed in an inert solvent such as tetrahydrofuran or diethyl ether at a temperature between −78° C. and 30° C. The preferred metallic derivative is the lithium derivative.

The compounds of formula (VIII) may be obtained by application or adaptation of the methods described in the examples.

The enantiomers of compounds of formula (I) containing at least one asymmetric site may be obtained synthetically from chiral precursors or by resolution of the racemates, e.g. by chromatography on a chiral column according to W. H. PIRCKLE et al., Asymmetric Synthesis, Vol. 1, Academic Press (1983).

The reaction mixtures obtained by the various processes described above are treated according to conventional physical methods (evaporation, extraction, distillation, crystallization, chromatography, etc.) or chemical methods (salt formation, etc.).

The compounds of formula (I) in free base form may be converted to an addition salt with acids by the action of an inorganic or organic acid in an organic solvent such as an alcohol, a ketone, a chlorinated solvent or an ether.

The compounds of formula (I) possess advantageous pharmacological properties. These compounds are inhibitors of 5HT uptake, and are hence useful in the treatment of depression, obsessional disorders, obesity and dietary behavioural disorders, in particular alcohol excess, as well as disorders of learning and of memory, panic attacks and pain.

The affinity of these products with respect to the paroxetine binding site (reflecting the inhibition of 5HT uptake) was measured by the method of E. HABERT et al., Eur. J. Pharmacol., 118, 107 (1985).

In this test, the compounds of formula (I) possess an IC₅₀ of less than 25 nM.

The compounds of formula (I) possess low toxicity. They are generally non-toxic at 300 mg/kg when given to mice orally in a single administration.

The compounds of formula (I) in which Het represents a piperidino radical substituted at the 4-position with a chain —$(CH_2)_m$—$R_2$ and $R_2$ represents a 5-fluoro-3-indolyl radical are especially advantageous.

Of special interest are the following products:

1{2-[4-((5-fluoro-3-indolyl)methyl)piperidino]ethyl} benzo[cd]indol-2-one

2-{3-[4-((5-fluoro-3-indolyl)methyl)piperidino]propyl} naphtho[1,8-cd]isothiazole 1,1-dioxide 2-{2-[4-((5-fluoro-3-indolyl)methyl)piperidino]ethyl}-2H-isothiazolo-[3,4,5-de]isoquinoline 1,1-dioxide 1-{2-[4-((5-fluoro-3-indolyl)methyl)piperidino]ethyl}-5,6-dihydro-1H,4H-1,2,5-thiadiazolo[4,3,2-ij]quinoline 2,2-dioxide 2-{2-[4-((5-fluoro-3-indolyl)methyl)piperidino]ethyl} naphtho[1,8-cd]isothiazole 1,1-dioxide 1-{2-[4-((5-fluoro-3-indolyl)methyl)piperidino]ethyl}-2-oxo-1,2,5,6-tetrahydro-4H-imidazo[4,5,1-ij]quinoline 3-methyl-1-{2-[4-((5-fluoro-3-indolyl)methyl)-piperidino]ethyl}-2H-benzimidazolin-2-one (RS)-2-{2-[4-((5-fluoro-3-indolyl)methyl)piperidino]ethyl}-3-methoxyisoindolinone (RS)-2-{2-[4-((5-fluoro-3-indolyl)methyl)piperidino]ethyl}isoindolinone For therapeutic application, use may be made of the compounds of formula (I) as they are or in the state of pharmaceutically acceptable salts.

As pharmaceutically acceptable salts, the addition salts with inorganic acids, such as hydrochlorides, sulphates, nitrates and phosphates, or organic acids, such as acetates, propionates, succinates, oxalates, benzoates, fumarates, maleates, methanesulphonates, isothionates, theophyllineacetates, salicylates, phenolphthalinates, methylenebis($\beta$-hydroxynaphthoates) or substitution derivatives of these derivatives, may be mentioned in particular.

EXAMPLES

The examples which follow, given without implied limitation, show how the invention may be put into practice.

EXAMPLE 1

A mixture of 2-(2-chloroethyl)naphtho[1,8-cd]isothiazole 1,1-dioxide (5.4 g), 4-[2-(3-indolyl)ethyl]piperidine (4.6 g) and sodium bicarbonate (1.7 g) in tetrahydrofuran (120 cc) and dimethylformamide (120 cc) is heated to boiling for 8 hours and then cooled to a temperature in the region of 20° C. The precipitate formed is separated by filtration, and the filtrate is evaporated to dryness at 40° C. under reduced pressure (20 mm Hg; 2.7 kPa). The residue obtained is purified by flash chromatography on a silica column under a stream of nitrogen at moderate pressure (0.5–1.5 bar) with ethyl acetate as eluent. After recrystallization in boiling acetonitrile, 2-{2-[4-(2-(3-indolyl)ethyl)piperidino]ethyl}naphtho[1,8-cd]isothiazole 1,1-dioxide (2.6 g), m.p. 169° C., is obtained.

2-(2-Chloroethyl)naphtho[1,8-cd]isothiazole 1,1-dioxide may be prepared in the following manner: a solution of 1,8-naphthosultam (82 g) in dimethylformamide (1000 cc) is added in the course of 2 hours to a 50% strength dispersion of sodium hydride (19.2 g) in liquid paraffin, through which a stream of argon is passed, while the temperature is maintained in the region of 35° C. The reaction medium is stirred for 1 hour at a temperature in the region of 20° C. and 1-bromo-2-chloroethane (35.2 cc) is then added. Stirring is maintained for 15 hours at a temperature in the region of 20° C. The reaction mixture is concentrated to dryness at 70° C. under reduced pressure (0.5 mm Hg; 0.07 kPa) and the residue is taken up with dichloromethane (1000 cc) and filtered. The filtrate is washed with water (4×1000 cc) and the organic phase is separated after settling has taken place, dried over anhydrous magnesium sulphate and evaporated to dryness at 40° C. under reduced pressure (20 mm Hg; 2.7 kPa). The oil obtained is purified by flash chromatography on a silica column under a stream of argon at moderate pressure (0.1–1.5 bar) with dichloromethane as eluent. 2-(2-Chloroethyl)-naphtho[1,8-cd]isothiazole 1,1-dioxide (70.2 g), m.p. 96° C., is obtained.

4-[2-(3-Indolyl)ethyl]piperidine may be prepared according to the method described by C. GUEREMY et al., J. Med. Chem., 23, 1306 (1980).

EXAMPLE 2

A mixture of 2-{2-[4-((5-fluoro-3-indolyl)methyl)-piperidino]ethyl}naphtho[1,8-cd]isothiazole 1,1-dioxide (2.3 g) in dimethylformamide (40 cc) is added in the course of 15 minutes to a 50% strength dispersion of sodium hydride (0.27 g) in liquid paraffin, under a stream of argon, while the temperature is maintained in the region of 20° C. The reaction medium is stirred for 1 hour at a temperature in the vicinity of 20° C. and a solution of methyl iodide (0.4 cc) in dioxane (20 cc) is then added in the course of 15 minutes. Stirring is maintained for 15 hours at a temperature in the vicinity of 20° C. The reaction mixture is taken up with distilled water (25 cc) and the organic phase is extracted with dichloromethane (4×50 cc), then washed with distilled water (25 cc), dried over anhydrous magnesium sulphate, filtered and concentrated to dryness at 40° C. under reduced pressure (20 mm Hg; 2.7 kPa). The residue obtained is purified by flash chromatography on a silica column under a stream of argon at moderate pressure (0.5–1.5 bar) with dichloromethane and then a mixture of ethyl acetate and methanol (97:3 by volume) as eluent. 2-{2-[4-((5-Fluoro-1-methyl-3-indolyl)methyl)piperidino]ethyl}naphtho[1,8-cd]isothiazole 1,1-dioxide (0.8 g) is obtained in the form of a yellow oil, which is converted to an acid oxalate, m.p. 150°–152° C.

2-{2-[4-((5-Fluoro-3-indolyl)methyl)piperidino]ethyl}naphtho[1,8-cd]isothiazole 1,1-dioxide may be prepared in the following manner: a mixture of 2-(2-chloroethyl)naphtho[1,8-cd]isothiazole 1,1-dioxide (5.3 g), 4-[(5-fluoro-3-indolyl)methyl]piperidine (4.6 g) and sodium bicarbonate (1.68 g) in tetrahydrofuran (120 cc) and dimethylformamide (120 cc) is heated to boiling for 48 hours and then cooled to a temperature in the region of 20° C. The precipitate formed is separated by filtration and the filtrate is evaporated to dryness at 40° C. under reduced pressure (20 mm Hg; 2.7 kPa). The residue obtained is purified by flash chromatography on a silica column under a stream of nitrogen at moderate pressure (0.5–1.5 bar) with ethyl acetate as eluent. A brown oil (4.4 g) is obtained. A portion (2 g) of this oil is recrystallized in boiling acetonitrile (15 cc). 2-{2-[4-((5-Fluoro-3-indolyl)methyl)piperidino]ethyl}naphtho[1,8-cd]isothiazole 1,1-dioxide (1.6 g), m.p. 161° C., is thereby obtained.

4-[(5-Fluoro-3-indolyl)methyl]piperidine may be prepared according to the method described by C. GUEREMY et al., J. Med. Chem., 23, 1306 (1980).

EXAMPLE 3

The procedure is as in Example 1, starting with 2-(2-chloroethyl)naphtho[1,8-cd]isothiazole 1,1-dioxide (2.7 g), 4-[2-(5-fluoro-3-indolyl)ethyl]piperidine (2.5 g) and sodium bicarbonate (0.8 g) in a mixture of dimethylformamide (80 cc) and tetrahydrofuran (40 cc). The mixture is heated to boiling for 9 hours and then cooled to a temperature in the region of 20° C. After purification by flash chromatography on a silica column under a stream of nitrogen at moderate pressure (0.5-1.5 bar) with ethyl acetate as eluent, and with recrystallization in boiling acetonitrile (15 cc), 2-{2-[4-(2-(5-fluoro-3-indolyl)ethyl)piperidino]ethyl}naphtho[1,8-cd]isothiazole 1,1-dioxide (1.7 g), m.p. 164° C., is obtained.

4-[2-(5-Fluoro-3-indolyl)ethyl]piperidine may be prepared according to the method described by C. GUEREMY et al., J. Med. Chem. 23, 1306 (1980).

EXAMPLE 4

The procedure is as in Example 1, starting with 2-(2-chloroethyl)naphtho[1,8-cd]isothiazole 1,1-dioxide (2 g), 4-[(5-fluoro-3-indolyl)methyl]-1,2,3,6-tetrahydropyridine hydrochloride (2 g) and sodium bicarbonate (1.3 g) in a mixture of dimethylformamide (70 cc) and tetrahydrofuran (45 cc). The mixture is heated to boiling for 20 hours and then cooled to a temperature in the region of 20° C. After purification by flash chromatography on a silica column under a stream of nitrogen at moderate pressure (0.5-1.5 bar) with dichloromethane and then ethyl acetate as eluents, 2-{2-[4-((5-fluoro-3-indolyl)methyl)-1,2,3,6-tetrahydro-1-pyridyl]ethyl}naphtho[1,8-cd]isothiazole 1,1-dioxide (0.4 g) is obtained in the form of a yellow oil, which is converted to an acid oxalate, m.p. 128° C.

4-[(5-Fluoro-3-indolyl)methyl]-1,2,3,6-tetrahydropyridine may be prepared in the following manner: 4-[(5-fluoro-3-indolyl)methyl]-1-vinyloxycarbonyl-1,2,3,6-tetrahydropyridine (11 g) and a 6.3N solution (100 cc) of hydrogen chloride in dioxane are stirred for 1 hour at a temperature in the vicinity of 20° C. The mixture is then concentrated to dryness at 40° C. under reduced pressure (20 mm Hg; 2.7 kPa). The residual oil is taken up with ethanol (40 cc) and the solution obtained is heated for 90 minutes to a temperature in the vicinity of 50° C. and then concentrated to dryness at 40° C. under reduced pressure (20 mm Hg; 2.7 kPa). The residue is taken up with isopropyl ether (50 cc); the precipitate formed is separated by filtration and purified by flash chromatography on a silica column under a stream of nitrogen at moderate pressure (0.5-1.5 bar) with a mixture of dichloromethane and methanol (90:10, then 80:20 by volume) as eluent. 4-[(5-Fluoro-3-indolyl)methyl]-1,2,3,6-tetrahydropyridine (3.3 g) is obtained in the form of a brown oil, which is used without further treatment in the subsequent syntheses.

4-[(5-Fluoro-3-indolyl)methyl]-1-vinyloxycarbonyl-1,2,3,6-tetrahydropyridine may be prepared in the following manner: vinyl chloroformate (3.8 cc) is added dropwise to a solution of 1-benzyl-4-[(5-fluoro-3-indolyl)methyl]-1,2,3,6-tetrahydropyridine (9 g) in dichloromethane (150 cc) while the temperature is maintained in the region of 10° C. The mixture is heated to boiling for 8 hours, cooled to a temperature in the vicinity of 20° C. and then concentrated to dryness at 20° C. under reduced pressure (20 mm Hg; 2.7 kPa). 4-[(5-Fluoro-3-indolyl)methyl]-1-vinyloxycarbonyl-1,2,3,6-tetrahydropyridine (11 g) is obtained, and is used in the crude state in the subsequent syntheses.

1-Benzyl-4-[(5-fluoro-3-indolyl)methyl]-1,2,3,6-tetrahydropyridine may be prepared in the following manner: sodium borohydride (1.4 g) is added, under a stream of argon, to a solution of 1-benzyl-4-[(5-fluoro-3-indolyl)methyl]pyridinium bromide (12 g) in ethanol (200 cc) while the temperature is kept in the vicinity of 25° C. Stirring is maintained for 36 hours at this temperature and distilled water (100 cc) is then added to the mixture. The organic phase is extracted with dichloromethane (4×50 cc), washed with distilled water (50 cc), dried over anhydrous magnesium sulphate and concentrated to dryness at 20° C. under reduced pressure (20 mm Hg; 2.7 kPa). 1-Benzyl-4-[(5-fluoro-3-indolyl)methyl]-1,2,3,6-tetrahydropyridine (9 g) is obtained in the form of a yellow oil, which is used in the crude state in the subsequent syntheses.

1-Benzyl-4-[(5-fluoro-3-indolyl)methyl]1,2,3,6-tetrahydropyridinium bromide may be prepared according to the method described by E. FRIEDERICHS et al., Arch. Pharm., 308, 209 (1975).

EXAMPLE 5

The procedure is as in Example 1, starting with 2-(2-chloroethyl)naphtho[1,8-cd]isothiazole 1,1-dioxide (2.4 g), 4-[(5-fluoro-3-indolyl)methyl]piperazine (2.2 g) and sodium bicarbonate (0.8 g) in a mixture of dimethylformamide (80 cc) and tetrahydrofuran (40 cc). The mixture is heated to boiling for 48 hours and then cooled to a temperature in the region of 20° C. After purification by flash chromatography on a silica column under a stream of nitrogen at moderate pressure (0.5-1.5 bar) with a mixture of ethyl acetate and methanol (90:10 by volume) as eluent, and recrystallization in boiling acetonitrile (7 cc), 2-{2-[4-((5-fluoro-3-indolyl)methyl)-piperazinyl]ethyl}naphtho[1,8-cd]isothiazole 1,1-dioxide (1 g), m.p. 85° C., is obtained.

4-[(5-Fluoro-3-indolyl)methyl]piperazine may be prepared according to the method described by C. S. RUNTY et al., Gazz. Chem. Ital., 81, 613 (1951) and A. O. M. STOPPANI, Revista Argentina Microbiologica, 19, 121 (1987).

EXAMPLE 6

The procedure is as in Example 1, starting with 2-(3-chloropropyl)naphtho[1,8-cd]isothiazole 1,1-dioxide (2.8 g), 4-[(5-fluoro-3-indolyl)methyl]piperidine (2.3 g) and sodium bicarbonate (0.8 g) in a mixture of dimethylformamide (90 cc) and tetrahydrofuran (60 cc). The mixture is heated to boiling for 24 hours and then cooled to a temperature in the region of 20° C. After purification by flash chromatography on a silica column under a stream of nitrogen at moderate pressure (0.5-1.5 bar) with ethyl acetate as eluent, and recrystallization a first time in acetonitrile (15 cc), and then a second time in boiling acetonitrile (5 cc), 2-{3-[4-((5-fluoro-3-indolyl)methyl)piperidino]propyl}naphtho[1,8-cd]isothiazole 1,1-dioxide (2.1 g), m.p. 100° C., is obtained.

2-(3-Chloropropyl)naphtho[1,8-cd]isothiazole 1,1-dioxide may be prepared in the following manner: a solution of 1,8-naphthosultam (175 g) in dimethylformamide (2100 cc) is introduced in the course of 3 hours 30 minutes into a 50% strength dispersion of sodium hydride (40.2 g) in liquid paraffin, under a stream of argon, while the temperature is maintained at between 20° C. and 30° C. The reaction medium is stirred for one hour at a temperature in the region of 20° C. and 1-bromo-3- chloropropane (83 cc) is then added in the course of 10 minutes. Stirring is maintained for 15 hours at a temperature in the region of 20° C. The reaction medium is concentrated to dryness at 50° C. under reduced pressure (0.5 mm Hg; 0.07 kPa). The residue is purified by flash chromatography on a silica column under a stream of nitrogen at moderate pressure (0.5-1.5 bar) with a mixture of dichloromethane and cyclohexane (60:40 by volume) as eluent. 2-(3-Chloropropyl)naphtho[1,8-cd]isothiazole 1,1-dioxide (165.7 g), m.p. 78° C., is obtained.

EXAMPLE 7

The procedure is as in Example 1, starting with 4-(1-indenylmethyl)piperidine (2.13 g), 2-(2-chloroethyl)-naphtho[1,8-cd]isothiazole 1,1-dioxide (2.94 g) and sodium hydrogen carbonate (0.92 g) in dimethylformamide (50 cc) and tetrahydrofuran (50 cc). The mixture is heated to boiling for 12 hours and then cooled to a temperature in the region of 20° C. After evaporating to dryness at 80° C. under reduced pressure (20 mm Hg; 2.7 kPa), the residue is taken up with water (50 cc) and extracted with dichloromethane (2×75 cc). The combined organic phases are dried over magnesium sulphate and taken to dryness at 80° C. under reduced pressure (20 mm Hg; 2.7 kPa). The residue is purified by flash chromatography on a silica column under nitrogen pressure at moderate pressure (0.5-1.5 bar) with a dichloromethane/methanol mixture (99:1 by volume) as eluent. A yellow oil (2.7 g) is obtained. Oxalic acid (0.54 g) in acetone (20 cc) is added to this oil. 2-{2-[4-(1-Indenylmethyl)piperidino]ethyl}naphtho[1,8-cd]isothiazole 1,1-dioxide (2.5 g) is thereby isolated in the form of an oxalate, m.p. 166° C.

4-(1-Indenylmethyl)piperidine may be prepared according to the method described by C. GUEREMY et al., Patent EP 42,322.

EXAMPLE 8

The procedure is as in Example 1, starting with 4-(1-indenylmethyl)piperidine (2.13 g), 2-(3-chloropropyl)-naphtho[1,8-cd]isothiazole 1,1-dioxide (3.37 g) and sodium hydrogen carbonate (1 g) in dimethylformamide (50 cc) and tetrahydrofuran (50 cc). The mixture is heated to boiling for 12 hours and then cooled to a temperature in the region of 20° C. After evaporation to dryness at 80° C. under reduced pressure (20 mm Hg; 2.7 kPa), the residue is taken up with water (50 cc) and extracted with dichloromethane (2×75 cc). The combined organic phases are dried over magnesium sulphate and taken to dryness at 80° C. under reduced pressure (20 mm Hg; 2.7 kPa). The residue is purified by flash chromatography on a silica column under nitrogen pressure at moderate pressure (0.5-1.5 bar) with a dichloromethane/methanol mixture (99:1 by volume) as eluent. A yellow oil (3.3 g) is obtained. Oxalic acid (0.67 g) in acetone (50 cc) is added to this oil. 2-{3-[4-(1-Indenylmethyl)piperidino]propyl}naphtho[1,8-cd]isothiazole 1,1-dioxide (3.5 g) is thereby isolated in the form of an oxalate, m.p. 140° C.

EXAMPLE 9

The procedure is as in Example 1, starting with 4-(1-indanylmethyl)piperidine (2.7 g), 2-(2-chloroethyl)naptho[1,8-cd]isothiazole 1,1-dioxide (3.2 g) and sodium hydrogen carbonate (2 g) in dimethylformamide (50 cc) and tetrahydrofuran (50 cc). The mixture is heated to boiling for 12 hours and then cooled to a temperature in the region of 50° C. After evaporating to dryness at 80° C. under reduced pressure (20 mm Hg; 2.7 kPa), the residue is taken up with water (25 cc) and extracted with dichloromethane (3×50 cc). The combined organic phases are dried over magnesium sulphate and taken to dryness at 80° C. under reduced pressure (20 mm Hg; 2.7 kPa). The residue is purified by flash chromatography on a silica column under nitrogen pressure at moderate pressure (0.5-1.5 bar) with a dichloromethane/methanol mixture (98:2 by volume) as eluent. A yellow oil (4.4 g) is obtained, and is recrystallized in boiling ethanol (50 cc). 2-{2-[4-(1-Indanylmethyl)-piperidino]ethyl}naphtho[1,8-cd]isothiazole 1,1-dioxide (2 g), m.p. 127° C., is thereby isolated.

4-(1-Indanylmethyl)piperidine may be prepared according to the method described by C. GUEREMY et al., Patent EP 42,322.

EXAMPLE 10

The procedure is as in Example 1, starting with 4-(1-indanylmethyl)piperidine (2.7 g), 2-(3-chloropropyl)-naphtho-[1,8-cd]isothiazole 1,1-dioxide (3.37 g) and sodium hydrogen carbonate (1 g) in dimethylformamide (50 cc) and tetrahydrofuran (50 cc). The mixture is heated to boiling for 24 hours and then cooled to a temperature in the region of 20° C. After evaporation to dryness at 80° C. under reduced pressure (20 mm Hg; 2.7 kPa), the residue is taken up with water (25 cc) and extracted with dichloromethane (2×75 cc). The combined organic phases are dried over magnesium sulphate and taken to dryness at 80° C. under reduced pressure (20 mm Hg; 2.7 kPa). The residue is purified by flash chromatography on a silica column under nitrogen at moderate pressure (0.5-1.5 bar) with a dichloromethane/methanol mixture (98:2 by volume) as eluent. A yellow oil (4.5 g) is obtained. Oxalic acid (0.88 g) in acetone (30 cc) is added to this oil. 2-{3-[4-(1-Indanylmethyl)piperidino]propyl}naphtho[1,8-cd]-isothiazole 1,1-dioxide (3.3 g) is thereby isolated in the form of an oxalate, m.p. 183° C.

EXAMPLE 11

The procedure is as in Example 1, starting with 4-(2-indanylmethyl)piperidine (1 g), 2-(2-chloroethyl)naphtho[1,8-cd]isothiazole 1,1-dioxide (1.2 g) and sodium hydrogen carbonate (0.72 g) in dimethylformamide (25 cc). The mixture is heated to boiling for 24 hours and then cooled to a temperature in the region of 20° C. After evaporation to dryness at 80° C. under reduced pressure (20 mm Hg; 2.7 kPa), the residue is taken up with water (25 cc) and extracted with dichloromethane (2×50 cc). The combined organic phases are dried over magnesium sulphate and taken to dryness at 80° C. under reduced pressure (20 mm Hg; 2.7 kPa). The residue is purified by flash chromatography on a silica column under nitrogen pressure at moderate pressure (0.5-1.5 bar) with a dichloromethane/methanol mixture (99:1 by volume) as eluent. A yellow solid (1 g) is obtained, and is recrystallized in boiling ethanol (40 cc). 2-{2-[4-(2-Indanylmethyl)piperidino]ethyl}naphtho[1,8-cd]isothiazole 1,1-dioxide (0.95 g), m.p. 126° C., is thereby isolated.

4-(2-Indanylmethyl)piperidine may be prepared according to the method described by C. GUEREMY, Patent EP 42,322.

EXAMPLE 12

The procedure is as in Example 1, starting with 4-(2-indenylmethyl)piperidine (1 g), 2-(2-chloroethyl)naphtho[1,8-cd]isothiazole 1,1-dioxide (1.2 g) and sodium hydrogen carbonate (0.71 g) in dimethylformamide (25 cc). The mixture is heated to boiling for 12 hours and then cooled to a temperature in the region of 20° C. After evaporation to dryness at 80° C. under reduced pressure (20 mm Hg; 2.7 kPa), the residue is taken up with water (25 cc) and extracted with dichloromethane (2×75 cc). The combined organic phases are dried over magnesium sulphate and taken to dryness at 80° C. under reduced pressure (20 mm Hg; 2.7 kPa). The residue is purified by flash chromatography on a silica column under nitrogen pressure at moderate pressure (0.5–1.5 bar) with a dichloromethane/methanol mixture (99:1 by volume) as eluent. A yellow oil (0.75 g) is obtained. Oxalic acid (0.15 g) in acetone (30 cc) is added to this oil. A yellow solid (0.9 g) is thereby isolated, and, on recrystallization in methanol (65 cc), yields 2-{2-[4-(2-indenylmethyl)piperidino]ethyl}naphtho[1,8-cd]isothiazole 1,1-dioxide (0.5 g) in the form of an oxalate, m.p. 176° C.

4-(2-Indenylmethyl)piperidine may be prepared according to the method described by C. GUEREMY et al., European Patent No. 42,322.

EXAMPLE 13

The procedure is as in Example 1, starting with 4-[(5-fluoro-2-indolyl)methylidene]piperidine (2.4 g), 2-(2-chloroethyl)naphtho[1,8-cd]isothiazole 1,1-dioxide (2.94 g) and sodium hydrogen carbonate (0.92 g) in tetrahydrofuran (50 cc) and dimethylformamide (25 cc). The mixture is heated to boiling for 12 hours and then cooled to a temperature in the region of 20° C. After evaporation to dryness at 80° C. under reduced pressure (20 mm Hg; 2.7 kPa), the residue is taken up with water (100 cc) and extracted with dichloromethane (2×75 cc). The combined organic phases are dried over magnesium sulphate and taken to dryness at 80° C. under reduced pressure (20 mm Hg; 2.7 kPa). The residue is purified by flash chromatography on a silica column under nitrogen at moderate pressure (0.5–1.5 bar) with a dichloromethane/methanol mixture (98:2 by volume) as eluent. A white meringue-like product (1.4 g) is obtained, and is recrystallized in boiling dichloromethane (25 cc) to give 2-{2-[4-((5-fluoro-2-indolyl)methylidene)piperidino]ethyl}-2H-naphtho-[1,8-cd]isothiazole 1,1-dioxide (0.9 g), m.p. 160° C.

4-[(5-Fluoro-2-indolyl)methylidene]piperidine may be prepared according to the method described by V. SNIECKUS, Can. J. Chem. 51, 792, (1973).

EXAMPLE 14

The procedure is as in Example 1, starting with 1-(2-chloroethyl)benzo[cd]indol-2-one (1.4 g), 4-[(5-fluoro-3-indolyl)methyl]piperidine (1.6 g) and sodium bicarbonate (1.5 g) in a mixture of dimethylformamide (20 cc) and tetrahydrofuran (15 cc). The mixture is heated to boiling for 48 hours and then cooled to a temperature in the region of 20° C. After purification by flash chromatography on a silica column under a stream of nitrogen at moderate pressure (0.5–1.5 bar) with ethyl acetate as eluent, and recrystallization in a mixture of cyclohexane (70 cc) and ethyl acetate (60 cc) at the boil, 1-{2-[4-((5-fluoro-3-indolyl)methyl)piperidino]ethyl}benzo[cd]indol-2-one (1 g), m.p. 156° C., is obtained.

1-(2-Chloroethyl)benzo[cd]indol-2-one may be prepared in the following manner: the procedure is as in Example 1 for the preparation of 2-(2-chloroethyl)naphtho[1,8-cd]isothiazole 1,1-dioxide, starting with a 50% strength dispersion of sodium hydride (1.1 g) in liquid paraffin, 1-bromo-2-chloroethane (1.9 cc) and benzo[cd]indol-2-one (4.1 g) in dimethylformamide (115 cc). The mixture is stirred for 18 hours at a temperature in the vicinity of 20° C. under a stream of argon. After purification by flash chromatography on a silica column under a stream of nitrogen at moderate pressure (0.5–1.5 bar) with a mixture of ethyl acetate and cyclohexane (70:30 by volume) as eluent, 1-(2-chloroethyl)benzo[cd]indol-2-one (1.4 g), m.p. 136° C., is obtained.

EXAMPLE 15

The procedure is as in Example 1, starting with 2-(2-chloroethyl)-3-phenyl-1,2-benzisothiazole 1,1-dioxide (2.85 g), 4-[(5-fluoro-3-indolyl)methyl]-piperidine (2.15 g) and sodium bicarbonate (2.3 g) in a mixture of dimethylformamide (30 cc) and tetrahydrofuran (20 cc). The mixture is heated to boiling for 48 hours and then cooled to a temperature in the region of 20° C. After purification by flash chromatography on a silica column under a stream of nitrogen at moderate pressure (0.5–1.5 bar) with a mixture of ethyl acetate and cyclohexane (80:20 by volume) as eluent, 2-{2-[4-((5-fluoro-3-indolyl)methyl)piperidino]ethyl}-3-phenyl-1,2-benzisothiazole 1,1-dioxide (2.6 g) is obtained, and is converted to a hydrochloride, m.p. 175° C.

2-(2-Chloroethyl)-3-phenyl-1,2-benzisothiazole 1,1-dioxide may be prepared in the following manner: the procedure is as in Example 1 for the preparation of 2-(2-chloroethyl)naphtho[1,8-cd]isothiazole 1,1-dioxide, starting with a 50% strength dispersion of sodium hydride (0.77 g) in liquid paraffin, 1-bromo-2-chloroethane (1.4 cc) and 3-phenyl-1,2-benzisothiazole 1,1-dioxide (4 g) in dimethylformamide (80 cc). The mixture is stirred for 18 hours at a temperature in the vicinity of 20° C. under a stream of nitrogen. After purification by flash chromatography on a silica column under a stream of nitrogen at moderate pressure (0.5–1.5 bar) with a mixture of ethyl acetate and cyclohexane (10:90 by volume) as eluent, 2-(2-chloroethyl)-3-phenyl-1,2-benzisothiazole 1,1-dioxide (3 g), m.p. 121° C., is obtained.

3-Phenyl-1,2-benzisothiazole 1,1-dioxide may be prepared in the following manner: N-tert-butyl-2-(α-hydroxybenzyl)benzenesulphonamide (10 g) is added to concentrated sulphuric acid solution (80 cc) cooled to 0° C. The mixture is then stirred for 1 hour at 25° C. and thereafter poured into ice-cold water (800 cc). After stirring for 1 hour, the precipitate is drained and then taken up with dichloromethane (100 cc). The organic solution is washed with water (2×50 cc), dried over magnesium sulphate and concentrated to dryness under reduced pressure (2.7 kPa). 3-Phenyl-1,2-benzisothiazole 1,1-dioxide (7.1 g), m.p. 118° C., is obtained.

N-tert-Butyl-2-(α-hydroxybenzyl)benzenesulphonamide may be prepared in the following manner: a 1.6M solution (64 cc) of N-butyllithium in hexane is added to a solution, cooled to 0° C., of N-tert-butylbenzenesulphonamide (8.5 g) in dry tetrahydrofuran (100 cc). After stirring for one hour, a solution of benzaldehyde (6.5 cc) in dry tetrahydrofuran (30 cc) is added and stirring is continued for 2 hours at 0° C. The mixture is treated with 2N hydrochloric acid (30 cc) and extracted with ethyl acetate (100 cc); the organic solution is washed with water (50 cc), dried over magnesium sulphate and concentrated to dryness under reduced pressure (2.7 kPa). The solid residue is washed with isopropyl ether (50 cc), drained and dried. N-tert-Butyl-2-(α-hydroxybenzyl)benzenesulphonamide (11.7 g), m.p. 160° C., is obtained.

N-tert-Butylbenzenesulphonamide may be prepared by the method described by J. G. LOMBARDINO, J. Org. Chem., 36, 1843, (1971).

EXAMPLE 16

The procedure is as in Example 1, starting with 2-(2-chloroethyl)-2H-isothiazolo[3,4,5-de]isoquinoline 1,1-dioxide (1.9 g), 4-[(5-fluoro-3-indolyl)methyl]piperidine (1.7 g) and sodium bicarbonate (1.8 g) in dimethylformamide (40 cc). The mixture is heated to boiling for 18 hours and then cooled to a temperature in the region of 20° C. After purification by flash chromatography on a silica column under a stream of nitrogen at moderate pressure (0.5-1.5 bar) with a mixture of ethyl acetate and methanol (80:20 by volume) as eluent, and recrystallization in boiling acetonitrile (160 cc), 2-{2-[4-((5-fluoro-3-indolyl)methyl)piperidino]ethyl}-2H-isothiazolo[3,4,5-de]isoquinoline 1,1-dioxide (0.52 g), m.p. 207° C., is obtained.

2-(2-Chloroethyl)-2H-isothiazolo[3,4,5-de]isoquinoline 1,1-dioxide may be prepared in the following manner: 2-bromo-1-chloroethane (1.5 cc) is added to a solution, cooled to 20° C., of the sodium salt of 2H-isothiazolo[3,4,5-de]isoquinoline 1,1-dioxide (obtained by heating, after the gaseous evolution has ceased, a solution of 4-bromo-5-isoquinolinesulphonamide (5.1 g) in dimethylformamide (30 cc) and a suspension of an 80% strength dispersion of sodium hydride (1.1 g) in liquid paraffin in dimethylformamide (50 cc) for 3 hours to 110° C.). The reaction medium is stirred for 2 hours 30 minutes at 110° C. and then 18 hours at a temperature in the vicinity of 20° C. The reaction mixture is concentrated to dryness at 50° C. under reduced pressure (0.5 mm Hg; 0.07 kPa). The residue is taken up with dichloromethane (500 cc); the organic phase is washed with distilled water (3×250 cc), separated after settling has taken place, dried over anhydrous magnesium sulphate, filtered and concentrated to dryness (20 mm Hg; 2.7 kPa). The residue obtained is purified by flash chromatography on a silica column under a stream of argon at moderate pressure (0.1-1.5 bar) with a mixture of ethyl acetate and cyclohexane (80:20 by volume) as eluent. 2-(2-Chloroethyl)-2H-isothiazolo[3,4,5-de]isoquinoline 1,1-dioxide (1.3 g) is obtained in the form of an orange-brown solid, which is used in the crude state in the subsequent syntheses.

4-Bromo-5-isoquinolinesulphonamide may be obtained in the following manner: ammonia is bubbled to saturation into dry tetrahydrofuran at −50° C. This solution is treated with a suspension of 4-bromo-5-isoquinolinesulphonyl chloride (8 g) in tetrahydrofuran (50 cc). The reaction mixture is allowed to return gradually to 20° C. The precipitate formed is drained, washed with tetrahydrofuran (3×10 cc), water (3×30 cc) and ethyl acetate (2×10 cc), then drained and dried. 4-Bromo-5-isoquinolinesulphonamide (4.5 g) is obtained in the form of a beige solid, the melting point of which is above 270° C.

4-Bromo-5-isoquinolinesulphonyl chloride may be obtained in the following manner: a solution of 5-amino-4-bromoisoquinoline (4.46 g) in hydrochloric acid (d=1.19) (44 cc) is cooled to −5° C. and then treated with a solution of sodium nitrite (1.93 g) in water (10 cc). The reaction mixture is stirred for 1 hour at 0° C. The solution obtained is poured into a saturated solution of sulphur dioxide in acetic acid (48 cc) to which a solution of cuprous chloride (0.65 g) in water (5.6 cc) has been added. The reaction mixture is stirred until the gaseous evolution has ceased and is then extracted with dichloromethane (2×100 cc). The organic phases are combined, washed with water, dried over magnesium sulphate and concentrated. 4-Bromo-5-isoquinolinesulphonyl chloride (5.6 g) is obtained in the form of a yellow solid, which is used without further treatment in the subsequent syntheses.

5-Amino-4-bromoisoquinoline may be prepared in the following manner: a suspension of 4-bromo-5-nitroisoquinoline (25.3 g) in 2N hydrochloric acid (180 cc) is added gradually to a solution of stannous chloride (90 g) in concentrated hydrochloric acid (d=1.19) (100 cc). The reaction mixture is heated to reflux for 90 minutes, then cooled and poured into 2N sodium hydroxide solution (2 liters) with stirring and cooling to about 0° C. The precipitate is washed with water, drained and dried. 5-Amino-4-bromoisoquinoline (21.6 g) is obtained in the form of yellow crystals, m.p. 155° C.

4-Bromo-5-nitroisoquinoline may be obtained by the process described by M. D. NAIR et al., Indian J. Chem. Soc., 5, 224 (1967).

EXAMPLE 17

An equimolecular mixture (3.6 g) of 4-(1-indanyl)piperidine and 4-(3-indenyl)piperidine, 2-(3-chloropropyl)naphtho[1,8-cd]isothiazole 1,1-dioxide (5.1 g) and sodium hydrogen carbonate (1.5 g) in dimethylformamide (50 cc) are brought to reflux for 7 hours. After the addition of water (50 cc) and dichloromethane (200 cc), drying of the organic phase over anhydrous magnesium sulphate and concentration to dryness at 80° C. under reduced pressure (20 mm Hg; 2.7 kPa), a brown oil (8.5 g) is isolated, and is purified by flash chromatography on a silica column under nitrogen pressure at moderate pressure (0.5-1.5 bar) with a dichloromethane/methanol mixture (97:3 by volume) as eluent. There are obtained, on the one hand a colorless oil (1.3 g) which, dissolved in acetone (35 cc) and with the addition of ethereal hydrogen chloride (4N), yields 2-{3-[4-(3-indenyl)piperidino]propyl}naphtho[1,8-cd]isothiazole 1,1-dioxide (1.5 g) in the form of a hydrochloride, m.p. 220° C., and on the other hand a colorless oil (1.6 g) which, dissolved in acetone (30 cc) and with the addition of ethereal hydrogen chloride (4N), yields 2-{3-[4-(1-indanyl)piperidino]propyl}naphtho[1,8-cd]isothiazole 1,1-dioxide (1.3 g) in the form of a hydrochloride, m.p. 237° C.

The equimolecular mixture of 4-(1-indanyl)piperidine and 4-(3-indenyl)piperidine may be prepared in the following manner: a mixture of 1-hydroxy-1-(4-pyridyl)indane (5.7 g), concentrated hydrochloric acid (12N) (2.5 cc), methanol (75 cc) and platinum oxide (0.5 g) is hydrogenated under a pressure of 5 bar at a temperature in the region of 25° C. for 5 hours. After filtration to remove the catalyst, addition of water (20 cc), extraction with dichloromethane (100 cc), drying of the organic phase over anhydrous magnesium sulphate and concentration to dryness at 50° C. under reduced pressure (20 mm Hg; 2.7 kPa), a brown oil (5 g) is isolated, and is purified by flash chromatography on silica under nitrogen pressure at moderate pressure (0.5-1.5 bar) with a dichloromethane/methanol mixture (90:10 by volume) as eluent. A colorless oil (4 g) is thereby obtained, which oil is a mixture of 4-(1-indanyl)piperidine and 4-(3-indenyl)piperidine in an equimolecular ratio, determined by proton NMR (250 MHz) in deuterated chloroform. This oil is used without further treatment in the subsequent syntheses.

1-Hydroxy-1-(4-pyridyl)indane may be prepared in the following manner: n-butyllithium (1.6M in hexane) (40.6 cc) is added to a solution of 4-bromopyridine (7.8 g) in diethyl ether (35 cc) at −78° C. The reaction medium is left for 1 hour at −40° C. 1-Indanone (6.6 g), dissolved in diethyl ether (25 cc), is then added and the mixture is stirred for 12 hours at a temperature in the vicinity of 25° C. After the addition of water (50 cc), extraction with dichloromethane (3×75 cc), drying of the combined organic phases over anhydrous magnesium sulphate and concentration to dryness at 50° C. under reduced pressure (20 mm Hg: 2.7 kPa), a yellow oil (11.8 g) is isolated, which oil, purified by flash chromatography on silica under a stream of nitrogen at moderate pressure (0.5-1.5 bar) with a dichloromethane/methanol mixture (98:2 by volume) as eluent, gives 1-hydroxy-1-(4-pyridyl)indane (5.7 g), m.p. 151° C.

EXAMPLE 18

A mixture of 4-(8-fluoro-1,2,3,4-tetrahydro-5H-pyrido[4,3-b]indol-2-ylmethyl)piperidine (1 g), 2-(2-chloroethyl)naphtho[1,8-cd]isothiazole 1,1-dioxide (0.94 g) and sodium hydrogen carbonate (0.59 g) in 1,3-dimethyl-2-imidazolidinone (25 cc) is brought to 150° C. for 16 hours. After return to a temperature in the vicinity of 25° C., this solution is poured into water (75 cc) and the mixture is extracted with ethyl acetate (3×75 cc). The combined organic phases are dried over magnesium sulphate and taken to dryness at 80° C. under reduced pressure (20 mm Hg: 2.7 kPa). The residue is purified by flash chromatography on a silica column under nitrogen at moderate pressure (0.5-1.5 bar) with a dichloromethane/methanol mixture (90:10 by volume) as eluent. 2-{2-[4-(8-Fluoro-1,2,3,4-tetrahydro-5H-pyrido[4,3-b]indol-2-ylmethyl)piperidino]ethyl}naphtho[1,8-cd]isothiazole 1,1-dioxide (0.35 g), m.p. 228° C., is obtained.

4-(8-Fluoro-1,2,3,4-tetrahydro-5H-pyrido[4,3-b]-indol-2-ylmethyl)piperidine may be prepared in the following manner: 1-trityl-4-(8-fluoro-1,2,3,4-tetrahydro-5H-pyrido[4,3-indol-2-ylmethyl)piperidine (47.3 g), 5N hydrochloric acid (225 cc) and ethanol (450 cc) are stirred for 12 hours at a temperature in the vicinity of 25° C. The mixture is concentrated to dryness at 40° C. under reduced pressure (20 mm Hg: 2.7 kPa). Water (270 cc) is added to the oil thereby obtained and the mixture is then extracted with diethyl ether (50 cc). The aqueous phase is neutralized with concentrated sodium hydroxide (10N) and extracted with ethyl acetate (2×300 cc). The combined organic phases are dried over anhydrous magnesium sulphate and concentrated to dryness at 50° C. under reduced pressure (20 mm Hg: 2.7 kPa). A yellow solid (13.7 g) is thereby isolated, and is purified by flash chromatography on a silica column under nitrogen at moderate pressure (0.5-1.5 bar) with an ethyl acetate/methanol/triethylamine mixture (70:29:1 by volume) as eluent. 4-(8-Fluoro-1,2,3,4-tetrahydro-5H-pyrido[4,3-b]-indol-2-ylmethyl)piperidine (6 g), taking the form of a yellow meringue-like product, is obtained, and is used without further treatment in the subsequent syntheses.

1-Trityl-4-(8-fluoro-1,2,3,4-tetrahydro-5H-pyrido[4,3-b]indol-2-ylmethyl)piperidine may be prepared in the following manner: a mixture of 8-fluoro-1,2,3,4-tetrahydro-5H-pyrido[4,3-b]indole (17 g), 1-trityl-4-(para-toluenesulphonyloxymethyl)piperidine (45.7 g), potassium carbonate (24.7 g) and dimethylformamide (225 cc) is heated to 100° C. for 5 hours. After return to a temperature in the region of 25° C., water (90 cc) is added and the mixture is extracted with ethyl acetate (450 cc). The organic phase is dried over anhydrous magnesium sulphate. After concentration to dryness at 50° C. under reduced pressure (20 mm Hg: 2.7 kPa), 1-trityl-4-(8-fluoro-1,2,3,4-tetrahydro-5H-pyrido-[4,3-b]indol-2-ylmethyl)piperidine (77.6 g), taking the form of a yellow meringue-like product, is isolated, and is used directly without further purification.

1-Trityl-4-(para-toluenesulphonyloxymethyl)piperidine may be prepared according to the method described by C. GUEREMY, Patent EP 42,322.

8-Fluoro-1,2,3,4-tetrahydro-5H-pyrido[4,3-b]indole may be prepared according to the method described by J. J. PLATTNER, patent U.S. Pat. No. 4,001,263.

EXAMPLE 19

A mixture of 4-(3-quinolylmethyl)piperidine (0.9 g), 2-(2-chloroethyl)naphtho[1,8-cd]isothiazole 1,1-dioxide (0.8 g), sodium hydrogen carbonate (0.67 g) and sodium iodide (0.6 g) in 1,3-dimethyl-2-imidazolidinone (25 cc) is brought to 150° C. for 16 hours. After return to a temperature in the vicinity of 25° C., this solution is poured into water (75 cc) and the mixture is extracted with ethyl acetate (3×75 cc). The combined organic phases are dried over magnesium sulphate and taken to dryness at 80° C. under reduced pressure (20 mm Hg: 2.7 kPa). The residue is purified by flash chromatography on a silica column under nitrogen at moderate pressure (0.5-1.5 bar) with a dichloromethane/methanol mixture (98:2 by volume) as eluent. A yellow oil (0.52 g) is obtained, which oil, dissolved in acetone (10 cc) and with the addition of oxalic acid (0.2 g), gives 2-{2-[4-(3-quinolylmethyl)piperidino]ethyl}naphtho[1,8-cd]isothiazole 1,1-dioxide (0.55 g) in the form of an oxalate, m.p. 150° C.

4-(3-Quinolylmethyl)piperidine may be prepared in the following manner: a mixture of 1-benzoyl-4-[(3-quinolyl)carbonyl]piperidine (5.5 g), diethylene glycol (75 cc) and hydrazine monohydrate (6 g) is heated to 100° C. for 3 hours. Potassium hydroxide (5 g) is then added at this temperature and the temperature is raised to 160° C. for 2 hours. After cooling to a temperature in the vicinity of 25° C., the reaction mixture is introduced into water (200 cc). After extraction with dichloromethane (100 cc), drying of the organic phase over anhydrous magnesium sulphate and concentration, an oil is obtained, and is purified by chromatography on silica under a pressure of 10 bar with a toluene/diethylamine/ethanol mixture (80:10:10 by volume) as eluent. The colorless oil (3 g) in the presence of ethanolic hydrogen chloride gives 4-(3-quinolylmethyl)piperidine (1.9 g) in the form of a hydrochloride, m.p. 265° C.

1-Benzoyl-4-[(3-quinolyl)carbonyl]piperidine may be prepared in the following manner: to a solution of 3-bromoquinoline (33.28 g) in diethyl ether (320 cc), there are added at −78° C., in the course of 30 minutes, n-butyllithium (1.6M in hexane) (100 cc) and then ethyl 1-benzoylisonipecotate (41.7 g) dissolved in tetrahydrofuran (320 cc). After return to a temperature in the vicinity of 25° C., the mixture is left for 1 hour at this temperature and water (30 cc) is then added. After extraction with ethyl acetate (100 cc), drying of the organic phase over anhydrous magnesium sulphate and concentration, an oil is obtained, and is purified by chromatography on silica under a pressure of 10 bar with ethyl acetate as eluent. 1-Benzoyl-4-[(3-quinolyl)-carbonyl]piperidine (10.3 g), m.p. 170° C., is thereby isolated.

Ethyl 1-benzoylisonipecotate was obtained by the benzoylation of ethyl isonipecotate with benzoyl chloride.

EXAMPLE 20

A mixture of 4-(3-chromanylmethyl)piperidine (1.8 g), 2-(2-chloroethyl)naphtho[1,8-cd]isothiazole 1,1-dioxide (1.8 g), sodium hydrogen carbonate (1.68 g) and sodium iodide (1 g) in 1,3-dimethyl-2-imidazolidinone (25 cc) is brought to 150° C. for 16 hours. After return to a temperature in the vicinity of 25° C., this solution is poured into water (75 cc) and the mixture is extracted with ethyl acetate (3×75 cc). The combined organic phases are dried over magnesium sulphate and taken to dryness at 80° C. under reduced pressure (20 mm Hg: 2.7 kPa). The residue is purified by flash chromatography on a silica column under nitrogen at moderate pressure (0.5-1.5 bar) with a dichloromethane/methanol mixture (99:1 by volume) as eluent. A yellow oil (1.9 g) is obtained, which oil, dissolved in acetone (30 cc) and with the addition of oxalic acid (0.37 g), gives a yellow solid (1.6 g) which is recrystallized in boiling dimethylformamide (20 cc), yielding 2-{2-[4-(3-chromanylmethyl)piperidino]ethyl}naphtho[1,8-cd]-isothiazole 1,1-dioxide (1.4 g) in the form of an oxalate, m.p. 230° C.

4-(3-Chromanylmethyl)piperidine may be prepared in the following manner: a solution of 3-(4-pyridyl)-methylene-4-chromanone (14 g) in acetic acid (140 cc) is hydrogenated in the presence of palladium on charcoal (10%) at a temperature in the vicinity of 25° C. and at atmospheric pressure for 5 hours. 4-(3-Chromanylmethyl)piperidine (13 g), taking the form of a yellow oil, is obtained, and is used without further purification.

3-(4-Pyridyl)methylene-4-chromanone may be prepared in the following manner: a mixture of 4-chromanone (30 g), 4-pyridinecarbaldehyde (42.8 g), concentrated sodium hydroxide (10N) (30 cc), methanol (100 cc) and water (60 cc) is stirred for 2 hours at a temperature in the vicinity of 10° C. 3-(4-Pyridyl)methylene-4-chromanone (9.2 g), m.p. 132° C., is thereby isolated directly.

EXAMPLE 21

A mixture of 4-(1,2,3,4-tetrahydro-3-quinolylmethyl)-piperidine (1.4 g), 2-(2-chloroethyl)naphtho[1,8-cd]isothiazole 1,1-dioxide (1.4 g), sodium hydrogen carbonate (1.3 g) and sodium iodide (0.78 g) in 1,3-dimethyl-2-imidazolidinone (25 cc) is brought to 150° C. for 16 hours. After return to a temperature in the vicinity of 25° C., this solution is poured into water (75 cc) and the mixture is extracted with ethyl acetate (3×75 cc). The combined organic phases are dried over magnesium sulphate and taken to dryness at 80° C. under reduced pressure (20 mm Hg: 2.7 kPa). The residue is purified by flash chromatography on a silica column under nitrogen at moderate pressure (0.5-1.5 bar) with a dichloromethane/methanol mixture (99:1 by volume) as eluent. A yellow oil (2.3 g) is obtained, which oil, after dissolution in acetone (30 cc) and the addition of oxalic acid (0.47 g), gives a yellow solid (0.85 g). This solid is recrystallized in boiling dimethylformamide (15 cc) and yields 2-{2-[4-(1,2,3,4-tetrahydro-3-quinolylmethyl)-piperidino]ethyl}naphtho[1,8-cd]isothiazole 1,1-dioxide (0.53 g) in the form of an oxalate, m.p. 134° C.

4-(1,2,3,4-Tetrahydro-3-quinolylmethyl)piperidine may be prepared in the following manner: hydrazine monohydrate (5.1 cc) is added to 1-acetyl-3-(4-piperidylmethyl)-1,2,3,4-tetrahydro-4-quinolone (8.25 g) in diethylene glycol (25 cc) and the mixture is brought to 150° C. for 20 minutes. The temperature is then allowed to return to 110° C., potassium hydroxide pellets (4.9 g) are added and the mixture is heated to 195° C. for 1 hour. After cooling to a temperature in the vicinity of 50° C., water (200 cc) is added and the mixture is extracted with diethyl ether (3×100 cc). The combined organic phases are dried over anhydrous magnesium sulphate and concentrated to dryness at 40° C. under reduced pressure (20 mm Hg: 2.7 kPa). A yellow resin (3.6 g) is isolated, which resin, dissolved in ethanol (18 cc) and with the addition of 7N ethereal hydrogen chloride (2.2 cc), gives 4-(1,2,3,4-tetrahydro-3-quinolylmethyl)piperidine (2.5 g) in the form of a hydrochloride, m.p. 220° C.

1-Acetyl-3-(4-piperidylmethyl)-1,2,3,4-tetrahydro-4-quinolone may be prepared in the following manner: 3-(4-pyridylmethylene)-1-acetyl-1,2,3,4-tetrahydro-4-quinolone (9.3 g), dissolved in acetic acid (95 cc), is hydrogenated in the presence of platinum oxide (0.93 g) at atmospheric pressure for 1 hour. The desired compound (8.25 g), taking the form of a yellow resin, is obtained, and is used without further treatment in the subsequent syntheses.

3-(4-Pyridylmethylene)-1-acetyl-1,2,3,4-tetrahydro-4-quinolone may be prepared in the following manner: 1-acetyl-1,2,3,4-tetrahydro-4-quinolone (15.4 g) is introduced into a solution of water (25 cc), methanol (40 cc) and 2N sodium hydroxide (12.5 cc). 4-Pyridinecarbaldehyde (17.5 g) is added at 0° C. After 12 hours at 0° C., the precipitate formed is filtered off and 3-(4-pyridylmethylene)-1-acetyl-1,2,3,4-tetrahydro-4-quinolone (6.8 g), m.p. 170° C., is thereby isolated.

1-Acetyl-1,2,3,4-tetrahydro-4-quinolone may be prepared in the following manner: a mixture of 1,2,3,4-tetrahydro-4-quinolone (4 g) and acetic anhydride (12 cc) is heated to reflux for 1 hour. After neutralization with concentrated sodium hydroxide (10N), extraction with diethyl ether, drying over anhydrous magnesium sulphate and concentration, a yellow solid (4.2 g), m.p. 89° C., is isolated.

1,2,3,4-Tetrahydro-4-quinolone may be prepared according to the method described by R. C. ELDERFIELD, J. Am. Chem. Soc., 71, 1901 (1949).

EXAMPLE 22

A mixture of 4-[(7-fluoro-1,2,3,4-tetrahydro-2-naphthyl)methyl]piperidine (1.3 g), 2-(2-chloroethyl)naphtho[1,8-cd]isothiazole 1,1-dioxide (1.22 g), sodium hydrogen carbonate (1.15 g) and sodium iodide (0.69 g) in 1,3-dimethyl-2-imidazolidinone (25 cc) is brought to 150° C. for 16 hours. After return to a temperature in the vicinity of 25° C., this solution is poured into water (75 cc) and the mixture is extracted with ethyl acetate (3×75 cc). The combined organic phases are dried over magnesium sulphate and taken to dryness at 80° C. under reduced pressure (20 mm Hg: 2.7 kPa). The residue is purified by flash chromatography on a silica column under nitrogen pressure at moderate pressure (0.5-1.5 bar) with a dichloromethane/methanol mixture (99:1 by volume) as eluent. A brown oil (1.7 g) is obtained, which oil, dissolved in acetone (10 cc) and with the addition of oxalic acid (0.41 g), gives a yellow solid (1.3 g). This solid is recrystallized in boiling dimethylformamide (13 cc) and yields 2-{2-[4-((7-fluoro-1,2,3,4-tetrahydro-2-naphthyl)methyl)piperidino]ethyl}naphtho[1,8-cd]isothiazole 1,1-dioxide (1.05 g) in the form of an oxalate, m.p. 265° C.

4-[(7-Fluoro-1,2,3,4-tetrahydro-2-naphthyl)methyl]-piperidine is obtained by heating a mixture of 4-[(7-fluoro-1,2,3,4-tetrahydro-1-oxo-2-naphthyl)methyl]-piperidine (13.1 g) and hydrazine monohydrate (9.4 g) in diethylene glycol (75 cc) to 160° C. for 15 minutes. The temperature is then allowed to return to 120° C., potassium hydroxide (8.4 g) is added and the mixture is heated to 160° C. for 5 hours. After return to a temperature in the vicinity of 25° C., water (650 cc) is added and the mixture is extracted with chloroform (350 cc). The combined organic phases are dried over anhydrous magnesium sulphate and concentrated to dryness at 50° C. under reduced pressure (20 mm Hg: 2.7 kPa). A yellow oil (14.5 g) is thereby isolated, and is purified by chromatography on silica with a toluene/diethylamine mixture (4:1 by volume) as eluent. A colorless oil (3.78 g) is isolated, which oil, dissolved in diethyl ether (20 cc), crystallizes with 10.3N ethanolic hydrochloric acid solution (2 cc) and leads to the formation of 4-[(7-fluoro-1,2,3,4-tetrahydro-2-naphthyl)methyl]piperidine (3.1 g) in the form of a hydrochloride, m.p. 208° C.

4-[(7-Fluoro-1,2,3,4-tetrahydro-1-oxo-2-naphthyl)-methyl]piperidine may be prepared in the following manner: 7-fluoro-2-(4-pyridylmethylene)-1-tetralone (15.9 g) in acetic acid (230 cc) in the presence of platinum oxide (1.59 g) is hydrogenated at atmospheric pressure at a temperature of 35° C. for 6 hours. The expected compound (12.6 g), m.p. 224° C., is thereby obtained in the form of a hydrochloride.

7-Fluoro-2-(4-pyridylmethylene)-1-tetralone may be prepared in the following manner: a mixture of 7-fluoro-2-(4-pyridyl)hydroxymethyl-1-tetralone (75 g), concentrated hydrochloric acid (10N) (830 cc) and 98% strength formic acid (270 cc) is heated to reflux for 3 hours. After neutralization with concentrated sodium hydroxide (10N), extraction with dichloromethane and concentration, a yellow solid (67.8 g) is isolated, which solid, recrystallized in a mixture of ethanol (600 cc) and methanol (230 cc), gives the desired compound (47.5 g), m.p. 144° C.

7-Fluoro-2-(4-pyridyl)hydroxymethyl-1-tetralone may be prepared in the following manner: 4-pyridinecarbaldehyde (59.2 g) is added to a mixture of 7-fluoro-1-tetralone (45.4 g), methanol (140 cc) and 2N sodium hydroxide (41.5 cc) at a temperature of 5° C. The mixture is stirred at a temperature in the vicinity of 25° C. for 3 hours. The expected compound (68.8 g), m.p. 133° C., is isolated directly.

7-Fluoro-1-tetralone may be prepared according to the method described by G. A. THIAULT, Bull. Soc. Chim. France, 1308 (1965).

EXAMPLE 23

A mixture of 4-[2-(1-indolyl)ethyl]piperidine (2 g), 2-(2-chloroethyl)naphtho[1,8-cd]isothiazole 1,1-dioxide (2 g), sodium hydrogen carbonate (1.26 g) and sodium iodide (1 g) in 1,3-dimethyl-2-imidazolidinone (25 cc) is brought to 150° C. for 16 hours. After return to a temperature in the vicinity of 25° C., this solution is poured into water (75 cc) and the mixture is extracted with ethyl acetate (3×75 cc). The combined organic phases are dried over magnesium sulphate and taken to dryness at 80° C. under reduced pressure (20 mm Hg: 2.7 kPa). The residue is purified by flash chromatography on a silica column under nitrogen at moderate pressure (0.5-1.5 bar) with a dichloromethane/methanol mixture (99:1 by volume) as eluent. A yellow oil (3.3 g), is obtained, which oil, after crystallization in boiling acetonitrile (30 cc) yields 2-{2-{4-[2-(1-indolyl)ethyl]-piperidino}ethyl}naphtho[1,8-cd]isothiazole 1,1-dioxide (1.52 g), m.p. 152° C.

4-[2-(1-Indolyl)ethyl]piperidine may be prepared in the following manner: a solution of 1-[2-(4-pyridyl)ethyl]indole (37 g) and platinum oxide (3.7 g) in acetic acid (350 cc) is hydrogenated at atmospheric pressure at a temperature in the vicinity of 25° C. for 10 hours, and yields 4-[2-(1-indolyl)ethyl]piperidine (33 g), the hydrochloride of which melts at 204° C.

1-[2-(4-Pyridyl)ethyl]indole may be prepared according to the method described by A. P. GRAY, J. Am. Chem. Soc. 79, 3554 (1957).

EXAMPLE 24 n-Butyllithium (1.6M) (25 cc) is introduced into a solution of indene (4.6 g) in tetrahydrofuran (100 cc) at a temperature in the region of −78° C., and the mixture is left for 45 minutes at this temperature. 2-[3-(4-Oxopiperidino)propyl]naphtho[1,8-cd]isothiazole 1,1-dioxide (13.7 g), dissolved in tetrahydrofuran (80 cc), is then added dropwise and the mixture is left stirring for 12 hours at a temperature in the region of 25° C. After the addition of water (160 cc), extraction with dichloromethane (500 cc), drying of the organic phase over anhydrous magnesium sulphate and concentration to dryness under reduced pressure at 50° C. (20 mm Hg: 2.7 kPa), an oil (18 g) is isolated, and is purified by flash chromatography on a silica column under a stream of nitrogen at moderate pressure (0.5-1.5 bar) with a dichloromethane/methanol mixture (98:2 by volume) as eluent. A yellow meringue-like product (5 g) is thereby isolated, which product, dissolved in diethyl ether (100 cc) and treated with 4N ethereal hydrogen chloride, yields 2-{3-[4-(1-indenylidene)piperidino]propyl}naphtho[1,8-cd]isothiazole 1,1-dioxide (4.4 g) in the form of a hydrochloride, m.p. 210° C.

2-[-3-(4-Oxopiperidino)propyl]naphtho[1,8-cd]isothiazole 1,1-dioxide may be prepared in the following manner: a mixture of 4-piperidone monohydrate (21.5 g), 2-(3-chloropropyl)naphtho[1,8-cd]isothiazole 1,1-dioxide (39.4 g) and sodium hydrogen carbonate (23.5 g) in dimethylformamide (420 cc) and tetrahydrofuran (420 cc) is brought to reflux for 16 hours. After return to a temperature in the vicinity of 25° C., filtration to remove the precipitate formed, addition of water (150 cc), extraction with dichloromethane (250 cc), drying of the organic phase over anhydrous magnesium sulphate and concentration to dryness at 40° C. under reduced pressure (20 mm Hg: 2.7 kPa), a yellow oil (48.6 g) is isolated, and is purified by flash chromatography on a silica column under a stream of nitrogen at moderate pressure (0.5-1.5 bar) with a dichloromethane/methanol mixture (99:1 by volume) as eluent. 2-[3-(4-Oxopiperidino)propyl]naphtho[1,8-cd]isothiazole 1,1-dioxide (36.2 g), m.p. 108° C., is thereby obtained.

EXAMPLE 25

A mixture of 2-(2-chloroethyl)naphtho[1,8-cd]isothiazole 1,1-dioxide (5.3 g), 4-[(5-fluoro-3-indolyl)methyl]piperidine (4.6 g) and sodium bicarbonate (1.68 g) in tetrahydrofuran (120 cc) and dimethylformamide (120 cc) is heated to boiling for 48 hours and then cooled to a temperature in the region of 20° C. The precipitate formed is separated by filtration and the filtrate is evaporated to dryness at 40° C. under reduced pressure (20 mm Hg; 2.7 kPa). The residue obtained is purified by flash chromatography on a silica column under a stream of argon at moderate pressure (0.5–1.5 bar) with ethyl acetate as eluent. A brown oil (4.4 g) is obtained. A portion (2 g) of this oil is recrystallized in boiling acetonitrile (15 cc). 2-{2-[4-((5-Fluoro-3-indolyl)methyl)piperidino]ethyl}naphtho[1,8-cd]isothiazole 1,1-dioxide (1.6 g), m.p. 161° C., is thereby obtained.

EXAMPLE 26

A mixture of 4-[(5-fluoro-2-indolyl)methyl]piperidine (2.9 g), 2-(2-chloroethyl)naphtho[1,8-cd]isothiazole 1,1-dioxide (3.5 g) and sodium hydrogen carbonate (1.1 g) in tetrahydrofuran (30 cc) and dimethylformamide (30 cc) is brought to reflux for 12 hours. After evaporation to dryness at 80° C. under reduced pressure (20 mm Hg; 2.7 kPa), the residue is taken up with water (150 cc) and extracted with ethyl acetate (2×75 cc). The combined organic phases are dried over magnesium sulphate and taken to dryness at 80° C. under reduced pressure (20 mm Hg; 2.7 kPa). The residue is purified by flash chromatography on a silica column under a stream of nitrogen at moderate pressure (0.5–1.5 bar) with a cyclohexane/ethyl acetate mixture (50:50 by volume) as eluent. 2-{2-[4-((5-Fluoro-2-indolyl)methyl)piperidino]ethyl} naphtho[1,8-cd]isothiazole 1,1-dioxide (2.3 g), m.p. 154° C., is obtained.

4-[(5-Fluoro-2-indolyl)methyl]piperidine may be prepared according to the method described by V. SNIECKUS, Can. J. Chem., 51, 792 (1973).

EXAMPLE 27

A mixture of 4-(3-indolylmethyl)piperidine (0.4 g), 2-(2-chloroethyl)naphtho[1,8-cd]isothiazole 1,1-dioxide (0.53 g), sodium hydrogen carbonate (0.17 g) and dimethylformamide (10 cc) is brought to reflux for 12 hours. After evaporation to dryness at 80° C. under reduced pressure (20 mm Hg; 2.7 kPa), the residue is taken up with water (30 cc) and extracted with ethyl acetate (2×50 cc). The combined organic phases are dried over magnesium sulphate and taken to dryness at 80° C. under reduced pressure (20 mm Hg; 2.7 kPa). The residue is purified by flash chromatography on a silica column under a stream of nitrogen at moderate pressure (0.5–1.5 bar) with a dichloromethane/methanol mixture (99:1 by volume) as eluent. 2-{2-[4-(3-Indolylmethyl)piperidino]ethyl}naphtho[1,8-cd]isothiazole 1,1-dioxide (0.4 g), m.p. 184° C., is obtained.

4-(3-Indolylmethyl)piperidine may be prepared according to the method described by C. GUEREMY, J. Med. Chem., 23, 1306 (1980).

EXAMPLE 28

The procedure is as in Example 25, starting with 1-(2-chloroethyl)-5,6-dihydro-1H,4H-1,2,5-thiadiazolo[4,3,2-ij]quinoline 2,2-dioxide (4.4 g), 4-[(5-fluoro-3-indolyl)methyl]piperidine (3.8 g) and sodium bicarbonate (4 g) in a mixture of dimethylformamide (50 cc) and tetrahydrofuran (30 cc). The mixture is heated to boiling for 36 hours and then cooled to a temperature in the region of 20° C. After purification by flash chromatography on a silica column under a stream of nitrogen at moderate pressure (0.5–1.5 bar) with ethyl acetate as eluent, and recrystallization in boiling acetonitrile (50 cc), 1-{2-[4-((5-fluoro-3-indolyl)methyl)piperidino]ethyl}-5,6-dihydro-1H,4H-1,2,5-thiadiazolo[4,3,2-ij]quinoline 2,2-dioxide (1 g), m.p. 149° C., is obtained.

1-(2-Chloroethyl)-5,6-dihydro-1H,4H-1,2,5-thiadiazolo[4,3,2-ij]quinoline 2,2-dioxide may be prepared in the following manner: the procedure is as in Example 1 for the preparation of 2-(2-chloroethyl)naphtho[1,8-cd]isothiazole 1,1-dioxide, starting with a 50% strength dispersion of sodium hydride (0.82 g) in liquid paraffin, 1-bromo-2-chloroethane (1.4 cc) and 5,6-dihydro-1H,4H-1,2,5-thiadiazolo[4,3,2-ij]quinoline 2,2-dioxide (3.6 g) in dimethylformamide (70 cc). The mixture is stirred for 48 hours at a temperature in the vicinity of 20° C. under a stream of argon. After the usual treatment, 1-(2-chloroethyl)-5,6-dihydro-1H,4H-1,2,5-thiadiazolo[4,3,2-ij]quinoline 2,2-dioxide (4.4 g) is obtained in the form of a brown oil, which is used in the crude state in the subsequent syntheses.

5,6-Dihydro-1H,4H-1,2,5-thiadiazolo[4,3,2-ij]quinoline 2,2-dioxide may be prepared in the following manner: sulphamide (6 g) is added to a solution of 8-amino-1,2,5,6-tetrahydroquinoline (9 g) in diglyme (90 cc). The mixture is heated to 160° C. for 90 minutes, then cooled an diluted in a mixture of water (300 cc) and ethyl acetate (300 cc). The organic phase is washed with water (3×300 cc), dried over magnesium sulphate and concentrated to dryness under reduced pressure (2.7 kPa). The residue is chromatographed on a silica column (particle size 0.2–0.063 mm, diameter 6 cm, height 60 cm), eluting under a pressure of 0.7 bar of nitrogen with a mixture of cyclohexane and ethyl acetate (80:20 by volume) and collecting 125-cc fractions. Fractions 12 to 22 are combined and concentrated to dryness under reduced pressure (2.7 kPa). 5,6-Dihydro-1H,4H-1,2,5-thiadiazolo[4,3,2-ij]quinoline 2,2-dioxide (9.4 g), m.p. 96° C., is thereby obtained.

8-Amino-1,2,5,6-tetrahydroquinoline may be prepared according to the method described by HAZLEWOOD et al., J. Pr. Soc., N. S. WALES, 71, 462 (1937–1938).

EXAMPLE 29

The procedure is as in Example 25, starting with 2-(2-chloroethyl)naphtho[1,8-cd]isothiazole 1,1-dioxide (4.1 g), 4-[(6-fluoro-3-indolyl)methyl]piperidine (3.6 g) and sodium bicarbonate (1.3 g) in a mixture of dimethylformamide (100 cc) and tetrahydrofuran (75 cc). The mixture is heated to boiling point for 8 hours and then maintained for 48 hours at a temperature in the region of 20°. After purification by flash chromatography on a silica column under a stream of nitrogen at moderate pressure (0.5–1.5 bar) with dichloromethane and then ethyl acetate as eluents, and recrystallization in boiling acetonitrile (40 cc), 2-{2-[4-((6-fluoro-3-indolyl)methyl)piperidino]ethyl}naphtho[1,8-cd]isothiazole 1,1-dioxide (1.2 g), m.p. 177° C., is obtained.

4-[(6-Fluoro-3-indolyl)methyl]-piperidine may be prepared according to the method described by C. GUEREMY et al., J. Med. Chem. 23, 1306 (1980).

EXAMPLE 30

The procedure is as in Example 25, starting with 2-(2-chloroethyl)naphtho[1,8-cd]isothiazole 1,1-dioxide (1.3 g), 4-[(4-fluoro-3-indolyl)methyl]piperidine hydrochloride (1.3 g) and sodium bicarbonate (1.3 g) in a mixture of dimethylformamide (15 cc) and tetrahydrofuran (10 cc). The mixture is heated to boiling for 48 hours and then cooled to a temperature in the region of 20° C. After purification by flash chromatography on a silica column under a stream of nitrogen at moderate pressure (0.5-1.5 bar) with ethyl acetate as eluent, and recrystallization in boiling isopropyl ether (200 cc), 2-{2-[4-((4-fluoro-3-indolyl)methyl)piperidino]ethyl}naphtho[1,8-cd]isothiazole 1,1-dioxide (0.8 g), m.p. 123° C., is obtained.

4-[2-(4-Fluoro-3-indolyl)methyl]piperidine may be prepared according to the method described by R. T. BORCHARDT et al., J. Het. Chem. 24, 1499 (1987).

EXAMPLE 31

The procedure is as in Example 25, starting with 1-(2-chloroethyl)-2-oxo-1,2,5,6-tetrahydro-4H-imidazo[4,5-ij]quinoline (6.9 g), 4-[(5-fluoro-3-indolyl)methyl]piperidine (6.8 g) and sodium bicarbonate (7.3 g) in a mixture of dimethylformamide (100 cc) and tetrahydrofuran (60 cc). The mixture is heated to boiling for 36 hours and then cooled to a temperature in the region of 20° C. After purification by flash chromatography on a silica column under a stream of nitrogen at moderate pressure (0.5-1.5 bar) with a mixture of ethyl acetate and methanol (90:10 by volume) as eluent, and recrystallization in boiling acetonitrile (150 cc), 1-{2-[4-((5-fluoro-3-indolyl)methyl)piperidino]ethyl}-2-oxo-1,2,5,6-tetrahydro-4H-imidazo[4,5,1-ij]quinoline (3.5 g), m.p. 177° C., is obtained.

1-(2-Chloroethyl)-2-oxo-1,2,5,6-tetrahydro-4H-imidazo[4,5,1-ij]quinoline may be prepared in the following manner: the procedure is as in Example 1 for the preparation of 2-(2-chloroethyl)naphtho[1,8-cd]isothiazole 1,1-dioxide, starting with a 50% strength dispersion of sodium hydride (2.54 g) in liquid paraffin, 1-bromo-2-chloroethane (4.4 cc) and 2-oxo-1,2,5,6-tetrahydro-4H-imidazo[4,5,1-ij]quinoline (9.3 g) in dimethylformamide (250 cc). The mixture is stirred for 48 hours at a temperature in the vicinity of 20° C. under a stream of argon. After purification by flash chromatography on a silica column under a stream of argon at moderate pressure (0.5-1.5 bar) with ethyl acetate as eluent, 1-(2-chloroethyl)-2-oxo-1,2,5,6-tetrahydro-4H-imidazo[4,5,1-ij]quinoline (6.9 g) is obtained in the form of an oil, which is used in the crude state in the subsequent syntheses.

2-Oxo-1,2,5,6-tetrahydro-4H-imidazo[4,5,1-ij]quinoline may be prepared in the following manner: the procedure is as in Example 28 for the preparation of 5,6-dihydro-1H,4H-1,2,5-thiadiazolo[4,3,2-ij]quinoline 2,2-dioxide, but starting with 8-amino-1,2,5,6-tetrahydroquinoline (12.6 g) and urea (6.5 g) in diglyme (150 cc). The mixture is heated to 160° C. for 4 hours; after the usual treatment and purification by flash chromatography on a silica column under a stream of argon at moderate pressure (0.5-1.5 bar) with ethyl acetate as eluent, 2-oxo-1,2,5,6-tetrahydro-4H-imidazo[4,5,1-ij]quinoline (8.4 g), m.p. 216° C., is obtained.

8-Amino-1,2,5,6-tetrahydroquinoline may be prepared according to the method described by HAZLEWOOD et al., J. Pr. Soc., N. S. WALES, 71, 462 (1937-1938).

EXAMPLE 32

Powdered zinc (2.97 g) is added at a temperature in the region of 20° C. to a stirred solution of (RS)-3-hydroxy-2-{2-[4-((5-fluoro-3-indolyl)methyl)piperidino]ethyl}isoindolinone (3.4 g) in acetic acid (21 cc). The mixture is heated to boiling for 9 hours and then cooled to a temperature in the vicinity of 20° C. After the addition of distilled water (30 cc), the solution is alkalinized to pH 7-8 with sodium bicarbonate. The organic phase is extracted with dichloromethane (4×30 cc), washed with distilled water (30 cc), dried over anhydrous magnesium sulphate, treated with vegetable charcoal, filtered and concentrated to dryness at 40° C. under reduced pressure (20 mm Hg; 2.7 kPa). The residue obtained is purified by flash chromatography on a silica column under a stream of argon at moderate pressure (0.5-1.5 bar) with ethyl acetate and then a mixture of ethyl acetate and methanol (98:2 by volume) as eluents. After recrystallization in ethyl acetate (40 cc), 2-{2-[4-((5-fluoro-3-indolyl)methyl)piperidino]ethyl}isoindolinone (0.54 g), m.p. 175° C., is obtained.

(RS)-3-Hydroxy-2-{2-[4-((5-fluoro-3-indolyl)methyl)piperidino]ethyl}isoindolinone may be prepared in the following manner: the procedure is as in Example 25, starting with (RS)-2-(2-bromoethyl)-3-hydroxyisoindolinone (5.5 g), 4-[(5-fluoro-3-indolyl)methyl]piperidine (5 g) and sodium bicarbonate (1.8 g) in a mixture of dimethylformamide (100 cc) and tetrahydrofuran (125 cc). The mixture is heated to boiling for 10 hours and then cooled to a temperature in the region of 20° C. After purification by flash chromatography on a silica column under a stream of nitrogen at moderate pressure (0.5-1.5 bar) with ethyl acetate and then an ethyl acetate/methanol mixture (98:2 by volume) as eluents, (RS)-3-hydroxy-2-{2-[4-((5-fluoro-3-indolyl)methyl)piperidino]ethyl}isoindolinone (5.4 g), m.p. 183° C., is obtained.

(RS)-2-(2-Bromoethyl)-3-hydroxyisoindolinone may be prepared in the following manner: potassium borohydride (10.5 g) is added in small portions at a temperature in the region of 20° C. to a solution of 2-(2-bromoethyl)phthalimide (50 g) in methanol (420 cc) and distilled water (42 cc). Stirring is maintained for 15 hours at a temperature in the vicinity of 20° C. and the reaction medium is then taken up with distilled water (250 cc). The organic phase is extracted with dichloromethane (4×100 cc), washed with distilled water (100 cc), dried over anhydrous magnesium sulphate, treated with vegetable charcoal, filtered and concentrated to dryness at 40° C. under reduced pressure (20 mm Hg; 2.7 kPa). The residue obtained is recrystallized in methyl ethyl ketone (70 cc). (RS)-2-(2-Bromoethyl)-3-hydroxyisoindolinone (17.3 g), m.p. 132° C., is obtained.

EXAMPLE 33

The procedure is as in Example 25, starting with (RS)-2-(2-bromoethyl)-3-methoxyisoindolinone (2.4 g), 4-[(5-fluoro-3-indolyl)methyl]piperidine (2.1 g) and sodium bicarbonate (0.74 g) in a mixture of dimethylformamide (50 cc) and tetrahydrofuran (40 cc). The mixture is heated to boiling for 10 hours and then cooled to a temperature in the region of 20° C. After purification by flash chromatography on a silica column under a stream of nitrogen at moderate pressure (0.5-1.5 bar) with ethyl acetate as eluent, and recrystallization a first time in acetonitrile (40 cc) and then in methyl ethyl ketone (35 cc). (RS)-2-{2-[4-((5-fluoro-3-indolyl)methyl)-piperidino]ethyl}-3-methoxyisoindolinone (0.8 g), m.p. 175° C., is obtained.

(RS)-2-(2-Bromoethyl)-3-methoxyisoindolinone may be prepared in the following manner: 36N sulphuric acid (19.8 cc) is added at a temperature in the vicinity of 0° C. to a stirred solution of (RS)-3-hydroxy-2-(2-bromoethyl)isoindolinone (2.8 g) in methanol (100 cc). The solution is heated to boiling for 5 hours and then cooled to a temperature in the vicinity of 20° C. The precipitate formed is filtered off and washed with methanol (30 cc). The filtrate is taken up with distilled water (20 cc) and 20% strength ammonia solution (20 cc). The organic phase is extracted with dichloromethane (4×40 cc), dried over anhydrous magnesium sulphate, treated with vegetable charcoal, filtered and concentrated to dryness at 40° C. under reduced pressure (20 mm Hg; 2.7 kPa). The residual oil is purified by flash chromatography on a silica column under a stream of argon at moderate pressure (0.1–1.5 bar) with dichloromethane as eluent. (RS)-2-(2-Bromoethyl)-3-methoxyisoindolinone (1.5 g) is obtained in the form of a yellow oil, which is used in the crude state in the subsequent syntheses.

EXAMPLE 34

The procedure is as in Example 25, starting with N-(2-chloroethyl)-N-methyl-2-napthalenesulphonamide (2.3 g), 4-[(5-fluoro-3-indolyl)methyl]piperidine (1.4 g) and sodium bicarbonate (1.5 g) in a mixture of dimethylformamide (60 cc) and tetrahydrofuran (40 cc). The mixture is heated to boiling for 36 hours and then cooled to a temperature in the region of 20° C. After purification by flash chromatography on a silica column under a stream of nitrogen at moderate pressure (0.5–1.5 bar) with ethyl acetate as eluent, and recrystallization in boiling acetonitrile (90 cc), N-{2-[4-((5-fluoro-3-indolyl)methyl)piperidino]ethyl}-N-methyl-2-naphthalenesulphonamide (1 g), m.p. 146° C., is obtained.

N-(2-Chloroethyl)-N-methyl-2-naphthalenesulphonamide may be prepared in the following manner: the procedure is as in Example 1 for the preparation of 2-(2-chloroethyl)naphtho[1,8-cd]isothiazole 1,1-dioxide, starting with a 50% strength dispersion of sodium hydride (0.77 g) in liquid paraffin, 1-bromo-2-chloroethane (2.25 cc) and N-methyl-2-naphthalenesulphonamide (5 g) in dimethylformamide (100 cc). The reaction medium is stirred for 5 hours at the boil under a stream of argon and then cooled to a temperature in the vicinity of 20° C. After purification by flash chromatography on a silica column under a stream of argon at moderate pressure (0.5–1.5 bar) with a cyclohexane/ethyl acetate mixture (80:20 by volume) as eluent, N-(2-chloroethyl)-N-methyl-2-naphthalenesulphonamide (2.3 g), m.p. 101° C., is obtained.

N-Methyl-2-naphthalenesulphonamide may be prepared in the following manner: methylamine gas (10 g) is condensed at −70° C. in a round-bottomed flask and tetrahydrofuran (50 cc) is then added. A solution of 2-naphthalenesulphonyl chloride (14.5 g) in tetrahydrofuran (50 cc) is then added at −70° C. Stirring is maintained for 2 hours 30 minutes, allowing the temperature to return to a temperature in the vicinity of 20° C. The reaction medium is taken up with ethyl acetate (200 cc) and distilled water (300 cc). The organic phase is separated after settling has taken place, dried over anhydrous magnesium sulphate, filtered and concentrated to dryness at 40° C. under reduced pressure (20 mm Hg; 2.7 kPa). N-Methyl-2-naphthalenesulphonamide (12.1 g), m.p. 137° C., is obtained.

EXAMPLE 35

6N hydrochloric acid (9.3 cc) is introduced at a temperature in the region of 20° C. into a solution of 3-isopropenyl-1-{2-[4-((5-fluoro-3-indolyl)methyl)-piperidino]ethyl}-2H-benzimidazol-2-one (4 g) in ethanol (50 cc). The solution is heated to boiling for 1 hour and then cooled to a temperature in the vicinity of 20° C. The reaction medium is taken up with dichloromethane (100 cc) and distilled water (30 cc) and alkalinized to pH 9 with 5N sodium hydroxide. The organic phase is extracted with dichloromethane (3×30 cc), washed with distilled water (90 cc), dried over anhydrous magnesium sulphate, treated with vegetable charcoal, filtered and concentrated to dryness at 40° C. under reduced pressure (20 mm Hg; 2.7 kPa). The residue is recrystallized in methyl ethyl ketone (15 cc). 1-{2-[4-((5-Fluoro-3-indolyl)methyl)piperidino]ethyl}-2H-benzimidazolin-2-one (0.4 g), m.p. 220° C., is obtained.

3-Isopropenyl-{2-[4-((5-fluoro-3-indolyl)methyl)-piperidino]ethyl}-2H-benzimidazolin-2-one may be prepared in the following manner: the procedure is as in Example 25, starting with 3-isopropenyl-1-(2-chloroethyl)-2H-benzimidazolin-2-one (2.4 g), 4-[(5-fluoro-3-indolyl)methyl]piperidine (2.3 g) and sodium bicarbonate (0.8 g) in a mixture of dimethylformamide (40 cc) and tetrahydrofuran (20 cc). The mixture is heated to boiling for 10 hours and then cooled to a temperature in the region of 20° C. After purification by flash chromatography on a silica column under a stream of nitrogen and moderate pressure (0.5–1.5 bar) with dichloromethane and ethyl acetate as eluents, 3-isopropenyl-1-{2-[4-((5-fluoro-3-indolyl)methyl)piperidino]ethyl}-2H-benzimidazolin-2-one (3 g), m.p. 132° C., is obtained.

1-(2-Chloroethyl)-3-isopropenyl-2H-benzimidazolin-2-one may be prepared in the following manner: the procedure is as in Example 1 for the preparation of 2-(2-chloroethyl)naphtho[1,8-cd]isothiazole 1,1-dioxide, starting with a 50% strength dispersion of sodium hydride (6.5 g) in liquid paraffin, 1-bromo-2-chloroethane (13.8 cc) and 1-isopropenyl-2H-benzimidazolin-2-one (25 g) in dimethylformamide (250 cc). The mixture is stirred for 48 hours at a temperature in the vicinity of 20° C. under a stream of argon. After purification by flash chromatography on a silica column under a stream of argon at moderate pressure (0.5–1.5 bar) with dichloromethane and then a dichloromethane/ethyl acetate mixture (90:10 by volume) as eluents, 1-(2-chloroethyl)-3-isopropenyl-2H-benzimidazolin-2-one (20.3 g) is obtained in the form of an oil, which is used in the crude state in the subsequent syntheses.

1-Isopropenyl-2H-benzimidazolin-2-one may be prepared according to the method described by O.METH-COHN et al., J. Chem. Soc., PERKIN TRANS I, 261 (1982).

EXAMPLE 36

The procedure is as in Example 25, starting with 1-(2-chloroethyl)-3-methyl-2H-benzimidazolin-2-one (2.7 g), 4-[(5-fluoro-3-indolyl)methyl]piperidine (3 g) and sodium bicarbonate (1.1 g) in a mixture of dimethylformamide (35 cc) and tetrahydrofuran (20 cc). The mixture is heated to boiling for 14 hours and then cooled to a temperature in the region of 20° C. After purification by flash chromatography on a silica column under a stream of nitrogen at moderate pressure (0.5–1.5 bar) with dichloromethane and then an ethyl acetate/methanol mixture (97:3 by volume) as eluents, and recrystallization in boiling acetonitrile (50 cc), 3-methyl-1-{2-[4-((5-fluoro-3-indolyl)methyl)piperidino]ethyl}-2H-benzimidazolin-2-one (1.9 g), m.p. 157° C., is obtained.

1-(2-Chloroethyl)-3-methyl-2H-benzimidazolin-2-one may be prepared according to U.S. Pat. No. 4,254,127.

The medicinal products according to the invention consist of a compound of formula (I), in free form or in the form of an addition salt with a pharmaceutically acceptable acid, in the pure state or in the form of a composition in which it is combined with any other pharmaceutically compatible product, which can be inert or physiologically active. The medicinal products according to the invention may be employed orally, parenterally, rectally or topically.

As solid compositions for oral administration, tablets, pills, powders (gelatin capsules, wafer capsules) or granules may be used. In these compositions, the active principle according to the invention is mixed with one or more inert diluents such as starch, cellulose, sucrose, lactose or silica, under a stream of argon. These compositions can also comprise substances other than diluents, e.g. one or more lubricants such as magnesium stearate or talc, a coloring, a coating (dragées) or a varnish.

As liquid compositions for oral administration, pharmaceutically acceptable solutions, suspensions, emulsions, syrups and elixirs, containing inert diluents such as water, ethanol, glycerol, vegetable oils or liquid paraffin, may be used. These compositions can comprise substances other than diluents, e.g. wetting products, sweeteners, thickeners, flavorings or stabilizers.

The sterile compositions for parenteral administration can preferably be solutions, aqueous or non-aqueous, suspensions or emulsions. As a solvent or vehicle, water, propylene glycol, a polyethylene glycol, vegetable oils, especially olive oil, injectable organic esters, e.g. ethyl oleate, or other suitable organic solvents may be employed. These compositions can also contain adjuvants, especially wetting agents, tonicity regulators, emulsifiers, dispersants and stabilizers. The sterilization may be carried out in several ways, e.g. by aseptic filtration, by incorporating sterilizing agents in the composition, by irradiation or by heating. They may also be prepared in the form of sterile solid compositions which can be dissolved at the time of use in sterile water or any other sterile injectable medium.

The compositions for rectal administration are suppositories or rectal capsules which contain, apart from the active product, excipients such as cocoa butter, semi-synthetic glycerides or polyethylene glycols.

The compositions for topical administration can be, e.g., creams, lotions, eyewashes, mouthwashes, nasal drops or aerosols.

In human therapy, the compounds according to the invention are especially useful for the treatment of depression, obsessional disorders, obesity, dietary behavioural disorders, in particular alcohol excess, disorders of learning and of memory, panic attacks and pain.

The dosages depend on the effect sought, the treatment period and the administration route used; they are generally between 50 and 300 mg per day administered orally for an adult, with single doses ranging from 25 to 100 mg of active substance.

Generally speaking, the doctor will determine the appropriate dosage in accordance with the age and weight and all other factors specific to the subject to be treated. The examples which follow illustrate some compositions according to the invention.

EXAMPLE A

Hard gelatin capsules containing 50 mg of active product and having the following composition are prepared according to the usual procedure:

| | |
|---|---|
| 1-{2-[4-((5-fluoro-3-indolyl)methyl)piperidino]ethyl}benzo[cd]indol-2-one | 50 mg |
| cellulose | 18 mg |
| lactose | 55 mg |
| colloidal silica | 1 mg |
| carboxymethylstarch sodium | 10 mg |
| talc | 10 mg |
| magnesium stearate | 1 mg |

EXAMPLE B

Tablets containing 50 mg of active product and having the following composition are prepared according to the usual procedure:

| | |
|---|---|
| 1-{2-[4-((5-fluoro-3-indolyl)methyl)piperidino]ethyl}-5,6-dihydro-1H,4H-1,2,5-thiadiazolo[4,3,2-ij]quinoline 2,2-dioxide | 50 mg |
| lactose | 104 mg |
| cellulose | 40 mg |
| polyvidone | 10 mg |
| carboxymethylstarch sodium | 22 mg |
| talc | 10 mg |
| magnesium stearate | 2 mg |
| colloidal silica | 2 mg |
| mixture of hydroxymethylcellulose, glycerol and titanium oxide (72:3.5:24.5) q.s. | 1 finished film-coated tablet weighing 245 mg |

EXAMPLE C

An injectable solution containing 10 mg of active product and having the following composition is prepared:

| | |
|---|---|
| 2-{3-[4-((1-indenyl)methyl)piperidino]propyl}naphtho[1,8-cd]isothiazole 1,1-dioxide | 10 mg |
| benzoic acid | 80 mg |
| benzyl alcohol | 0.06 cc |
| sodium benzoate | 80 mg |
| ethanol, 95% strength | 0.4 cc |
| sodium hydroxide | 24 mg |
| propylene glycol | 1.6 cc |
| water q.s. | 4 cc |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. A compound of formula:

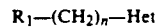

$$R_1-(CH_2)_n-Het \qquad (I)$$

in which $R_1$ represents a residue of formula:

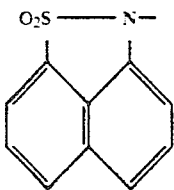
(A)

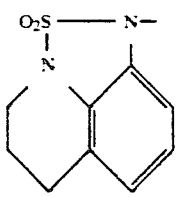
(B)

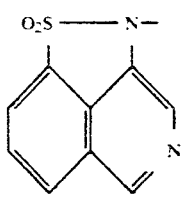
(C)

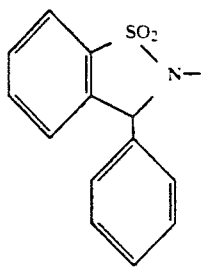
(D)

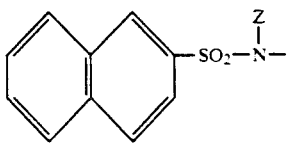
(J)

X represents a hydrogen atom or an alkyl radical,
Y represents a hydrogen atom or an alkyl or alkoxy radical,
Z represents an alkyl radical,
n is equal to 2 or 3,
Het represents a substituted piperidino (substituted at the 4-position with a 1-indenylidene, 1-indenyl or 1-indanyl radical or with a chain $-(CH_2)_m-R_2$ or $=CH-R_2$),
m is equal to 1 or 2, and
$R_2$ represents a 2- or 3-indolyl (optionally substituted with a halogen atom and/or on the nitrogen atom with an alkyl radical), 1- or 2-indanyl, 1- or 2-indenyl, or 1-indolyl radical, as well as its salts with inorganic or organic acids and its racemates and enantiomers when it contains at least one asymmetric center, it being understood that the alkyl and alkoxy radicals contain 1 to 4 carbon atoms in a straight or branched chain.

2. A compound of formula (I) according to claim 1, wherein the halogen atoms are fluorine atoms.

3. A compound of formula (I) according to claim 1 wherein Het represents a piperidino radical substituted at the 4-position with a chain $-(CH_2)_m-R_2$, and $R_2$ represents a 5-fluoro-3-indolyl radical.

4. 1-{2-[4-((5-Fluoro-3-indolyl)methyl)piperidino]ethyl{-5,6-dihydro-1H,4H-1,2,5-thiadiazolo[4,3,2-ij]quinoline 2,2-dioxide and its addition salts with an inorganic or organic acid.

5. A medicinal composition, which contains as active substance at least one compound of formula (I) according to claim 1 and an inert carrier.

6. A method of treatment for disorders associated with 5HT uptake which comprises treating a subject in need thereof with an effective amount of the composition of claim 5.